(12) United States Patent
Huang et al.

(10) Patent No.: US 10,334,850 B2
(45) Date of Patent: Jul. 2, 2019

(54) RECOMBINANT MICROORGANISM EXPRESSING AVERMECTIN ANALOGUE AND USE THEREOF

(71) Applicant: Zhejiang Hisun Pharmaceutical Co., Ltd., Zhejiang (CN)

(72) Inventors: Jun Huang, Zhejiang (CN); Jidong Wang, Zhejiang (CN); Anliang Chen, Zhejiang (CN); Aiwen Deng, Zhejiang (CN); Jiatan Lin, Zhejiang (CN); Zhen Yu, Zhejiang (CN); Meihong Li, Zhejiang (CN); Na Li, Zhejiang (CN); Haibin Wang, Zhejiang (CN); Linghui Zheng, Zhejiang (CN); Hua Bai, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 358 days.

(21) Appl. No.: 15/123,827

(22) PCT Filed: Apr. 28, 2014

(86) PCT No.: PCT/CN2014/076372
§ 371 (c)(1),
(2) Date: Sep. 6, 2016

(87) PCT Pub. No.: WO2015/135242
PCT Pub. Date: Sep. 17, 2015

(65) Prior Publication Data
US 2017/0013837 A1    Jan. 19, 2017

(30) Foreign Application Priority Data

Mar. 10, 2014    (CN) .......................... 2014 1 0085431

(51) Int. Cl.
| | | |
|---|---|---|
| *A01N 43/90* | (2006.01) | |
| *C12N 15/76* | (2006.01) | |
| *C12P 19/62* | (2006.01) | |
| *C12R 1/465* | (2006.01) | |

(52) U.S. Cl.
CPC ............. *A01N 43/90* (2013.01); *C12N 15/76* (2013.01); *C12P 19/623* (2013.01); *C12R 1/465* (2013.01)

(58) Field of Classification Search
None
See application file for complete search history.

(56) References Cited

U.S. PATENT DOCUMENTS

| | | |
|---|---|---|
| 5,234,831 A | 8/1993 | Hafner et al. |
| 2011/0201567 A1 | 8/2011 | Davies et al. |

FOREIGN PATENT DOCUMENTS

| | | |
|---|---|---|
| CN | 103834605 A | 6/2016 |
| DE | 40 31 039 A1 | 4/1991 |
| EP | 0 445 460 | 9/1991 |

OTHER PUBLICATIONS

EP 14885605.7, Nov. 8, 2017, Partial Supplementary European Search Report.
AU 2014386509, Jun. 8, 2017, Australian Office Action.
Australian Office Action dated Jun. 8, 2017 in connection with Application No. 2014386509.
Chen et al., Effect of gene disruption of aveD on avermectins production in Streptomyces avermitilis. Wei sheng wu xue bao (Acta Microbiologica Sinica), 2001, vol. 41, pp. 440-446.
Chen et al., Unusual metabolites produced by recombinant Streptomyces avermitilis after insertional inactivation into aveD gene. Chinese Journal of Antibiotics, 2009, vol. 1, pp. 18-23, 60.
He et al., Cloning of separate meilingmycin biosynthesis gene clusters by use of acyltransferase-ketoreductase didomain PCR amplification. Applied and Environmental Microbiology, May 2010, vol. 76, pp. 3283-3292.
Hong et al., Targeted gene disruption of the avermectin B O-methyltransferase gene in Streptomyces avermitilis. Biotechnology Letters, 2001, vol. 23, pp. 1765-1770.
Huang et al., Gene replacement for the generation of designed novel avermectin derivatives with enhanced acaricidal and nematicidal activities. Applied and Environmental Microbiology, 2015, vol. 81, pp. 5326-5334.
Kim et al., Engineered biosynthesis of milbemycins in the avermectin high-producing strain Streptomyces avermitilis. Microbial Cell Factories, 2017, vol. 16: 9. 16 pages.
Omura et al., Selective production of specific components of avermectins in Streptomyces avermitilis. The Journal of Antibiotics, May 1991, vol. 44, pp. 560-563.
Pang et al., Production of 6,8a-seco-6,8a-deoxy derivatives of avermectins by a mutant strain of Streptomyces avermitilis. The Journal of Antibiotics, Jan. 1995, vol. 48, pp. 59-66.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The present invention relates to a recombinant microorganism expressing avermectin or analogs thereof and construction method thereof, and also relates to a method of producing avermectin or analogs thereof using the recombinant microorganism, and avermectin or analogs thereof obtained using the method. In addition, the present invention further relates to uses of the avermectin or analogs thereof as insecticides. Using the recombinant microorganism of the present invention to produce avermectin or analogs thereof has numerous advantages, for example comprising at least one of the following: good stability, high yield, simple process, environmentally friendly, and greatly saving of production costs.

5 Claims, 10 Drawing Sheets
Specification includes a Sequence Listing.

(56) References Cited

OTHER PUBLICATIONS

Schulman et al., "Streptomyces avermitilis" mutants defective in methylation of avermectins. Antimicrobial Agents and Chemotherapy, May 1987, vol. 31, pp. 744-747.
Wang et al., Deletion analysis of aveD gene from a Streptomyces avermitilis mutant producing doramectin. China Biotechnology, 2010, vol. 30, pp. 46-51.
Zhang et al., Genetic engineering of Streptomyces bingchenggensis to produce milbemycins A3/A4 as main components and eliminate the biosynthesis of nanchangmycin. Applied Microbiology and Biotechnology, 2013, vol. 97, pp. 10091-10101.
Partial Supplementary European Search Report for Application No. 14885605.7 dated Nov. 8, 2017.
Japanese Office Action for Application No. 2016-555820 dated Sep. 5, 2017.
Tang et al., Site-directed Mutagenesis of Streptomyces avermitilis aveD Gene. Agricultural Science and Technology. 2011; 12(10): 1424-26.
Yong et al., Alternative Production of Avermectin Components in *Streptomyces avermitilis* by Gene Replacement. J. Microbio. Jun. 2005;43(3):277-84.
Zhi et al., Effect of Gene Deletion of aveD on Avermectins Production in Streptomyces avermitilis. Weishengwu Xuebao. Oct. 2002;42(5):534-8.
International Search Report, dated Dec. 1, 2014, from corresponding International Application No. PCT/CN2014/076372.
Zhu et al.: "Cloning, Sequence Analysis and Gene Replacement of an Avermectin C5—O methyltransferase Gene," (2013) Chinese Journal of Antibiotics; vol. 28(1); pp. 1-5.
Zhou et al.: "The Construction of Gene-engineered Strain Only Producing Avermectin B," (2010) Journal of Shenyang Pharmaceutical; vol. 27, 30; pp. 919-923.

RECOMBINANT MICROORGANISM EXPRESSING AVERMECTIN ANALOGUE AND USE THEREOF

CROSS REFERENCE TO RELATED APPLICATIONS

This application is the national phase of International Application No. PCT/CN2014/076372, filed on Apr. 28, 2014, which claims priority to Chinese Patent Application No. 201410085431.2 filed with the Chinese State Intellectual Property Office on Mar. 10, 2014, the entire disclosures of both applications are incorporated herein by reference to the maximum extent allowable by law.

FIELD OF THE INVENTION

The invention belongs to the field of genetic engineering and microbial fermentation, in particular to a recombinant microorganism expressing avermectin or analogues thereof and a method of producing avermectin or analogues thereof using the recombinant microorganism.

BACKGROUND OF THE INVENTION

Avermectins and ivermectin are excellent pesticides and veterinary drugs, which have got a wide range of use in the last three decades. Among these, avermectins belong to a class of macrolide derivatives having insect-resistant activity produced from the fermentation of *Streptomyces avermitilis*. Avermectins isolated from the fermentation products of *Streptomyces avermitilis* are composed of a series of structurally similar compounds existed in pairs, including component A and component B, wherein the activity of component B is higher than that of component A. Structurally, component A has a methoxy at C5 position of the macrocyclic lactone ring of avermectins, whereas component B has a hydroxyl group at the same position. As far as component B of avermectins is concerned, it includes two compounds existed in pairs, which are respectively called B1a and B1b and have the following structures:

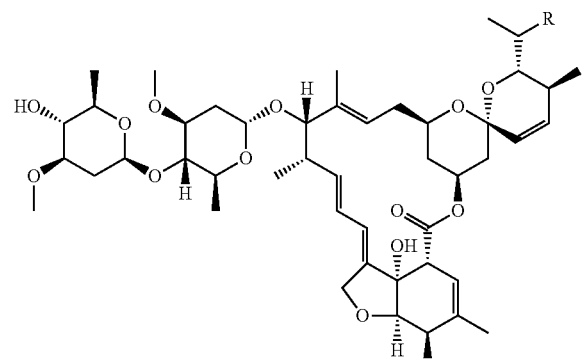

Avermectin $B_{1a}$: R = $CH_2CH_3$
Avermectin $B_{1b}$: R = $CH_3$

Commercially available pesticide of avermectins typically contains active ingredient of avermectins mainly composed of avermectins B1a and B1b. Ivermectin is obtained from structural modification of avermectin. But after nearly three decades of use, it will be phased out in the near future because of drug resistance problems. Milbemycin belongs to a new generation of avermectin analogues produced from the fermentation of *Streptomyces hygroscopicus*. The insect-resistant activity of milbemycin is stronger than those of avermectins and ivermectin, but the toxicity of milbemycin is greatly lower than both of them.

U.S. Pat. No. 4,134,973 discloses a carbohydrate derivative of milbemycin and 13-hydroxyl milbemycin and methods for their preparation through a series of chemical reactions, and confirms that these carbohydrate derivatives have insect-resistant activity. However, these chemical reactions require a series of complex processes and require special reaction raw materials, and will produce a series of by-products because of specificity that is not strong enough, which will bring about environmental problems and also increase the cost of production.

Therefore, there exists the need for an alternative method of producing avermectin or analogues thereof by biosynthetic methods.

SUMMARY OF THE INVENTION

One aspect of the invention is to provide a recombinant *Streptomyces* expressing avermectin or analogues thereof, wherein the recombinant *Streptomyces*

(1) has an inactivated or activity-decreased aveD gene; and/or (2) has an inactivated or activity-decreased aveAI gene, and has a functional milAI gene.

In one embodiment, the recombinant *Streptomyces* of the present invention is *Streptomyces avermitilis*, preferably *Streptomyces avermitilis* AD28 or *Streptomyces avermitilis* MA220, more preferably *Streptomyces avermitilis* MA220.

In another embodiment, the aveD gene is inactivated or activity-decreased by PCR targeting technology.

In another embodiment, the aveAI gene in the genome of *Streptomyces* is replaced by the functional milAI gene, so that the aveAI gene is inactivated or activity-decreased, and the *Streptomyces* is acquired with the functional milAI gene. In a particular embodiment, this replacement is implemented by intracellular genetic recombination.

Another aspect of the present invention is to provide a use of the recombinant *Streptomyces* of the present invention for the production of avermectin or analogues thereof.

In one embodiment, the avermectin or analogues thereof is avermectin B1a and avermectin B1b. In another embodiment, the avermectin or analogues thereof is tenvermectins, in particular tenvermectin A and tenvermectin B.

A third aspect of the present invention is to provide a method for producing avermectin or analogues thereof, comprising: culturing a recombinant *Streptomyces* of claim 1 or 2, and recovering avermectin or analogues thereof from the culture.

In one embodiment, the avermectin or analogues thereof are avermectin components B1a and B1b. In another embodiment, the avermectin or analogues thereof are tenvermectins, in particular tenvermectin A and tenvermectin B.

A fourth aspect of the present invention is to provide a method for constructing a recombinant *Streptomyces* of claim 1 or 2, said method comprising:

(1) providing a *Streptomyces* to be modified;

and the method further comprises at least one of the following steps:

(2) inactivating the aveD gene in the *Streptomyces* to be modified or decreasing the activity thereof; and (3) inactivating the aveAI gene in the *Streptomyces* to be modified or decreasing the activity thereof, and introducing the functional milAI gene into the *Streptomyces* to be modified.

In one embodiment, the *Streptomyces* to be modified is *Streptomyces avermitilis*, preferably *Streptomyces avermitilis* MA-4680.

In another embodiment, in step (2), the aveD gene is inactivated or activity-decreased by PCR targeting technology.

In another embodiment, in step (3), the aveAI gene in the genome of *Streptomyces* is replaced by the functional milAI gene, so that the aveAI gene is inactivated or activity-decreased, and the *Streptomyces* is acquired with the functional milAI gene.

A fifth aspect of the present invention also provides a use of avermectin or analogues thereof obtained according to the method of the present invention as insecticides.

The present disclosure is merely illustrative of some of the claimed embodiments, wherein one or more technical characteristics disclosed in one or more embodiments may be combined with any of one or more other embodiments, and these technical solutions obtained via combination are within the scope claimed by the present application, as if these technical solutions obtained via combination are specifically disclosed in the present disclosure.

Through at least one of the above aspects, the recombinant *Streptomyces* of the present invention can efficiently produce avermectin or analogues thereof. When used in the production of avermectin, it can specifically produce avermectins B1a and B1b, which are substantially free of avermectin component A, or contain significantly reduced amount of avermectin component A therein. When used in the production of avermectin analogues, the avermectin analogues may be tenvermectins, wherein the tenvermectins contain tenvermectin A and tenvermectin B. It is also noted that the present invention, when constructing recombinant *Streptomyces*, efficiently inactivates aveD gene by PCR targeting technology. Using the recombinant *Streptomyces* of the present invention to produce avermectin or analogues thereof by fermentation has good stability, high yield, are more environmentally friendly and simple compared with chemical synthesis methods, and also greatly saves production costs. Moreover, avermectin or analogues thereof obtained by the process of the present invention has significantly improved insect-resistant activity.

The present disclosure is merely illustrative of some of the claimed embodiments, wherein one or more technical characteristics disclosed in one or more embodiments may be combined with any of one or more other embodiments, and these technical solutions obtained via combination are within the scope claimed by the present application, as if these technical solutions obtained via combination are specifically disclosed in the present disclosure.

DESCRIPTION OF THE DRAWINGS

The present invention is illustrated by the accompanying drawings in conjunction with the additional detailed description hereinafter. It needs to be noted that the following description is merely illustrative of the technical solutions claimed by the present invention, and is without any limitation on these technical solutions. The scope of the present invention is dictated by the contents disclosed by the appended claims.

DETAILED EMBODIMENTS

Figure 1:
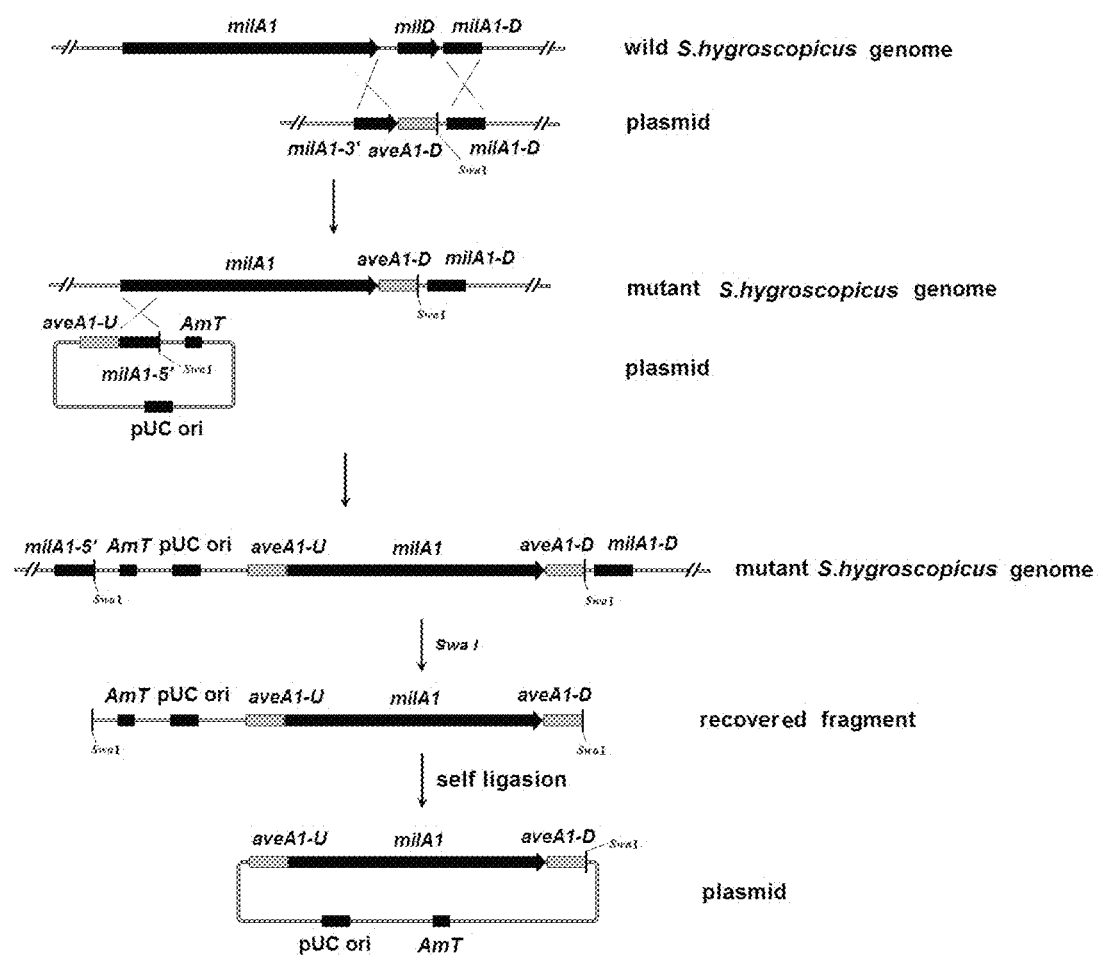
FIG. 1: The schematic diagram of constructing recombinant plasmid using in vivo recombination system of *Streptomyces hygroscopicus*.

The terms as used in the present application have the same meanings as those of the terms in the prior art. In order to clearly show the meanings of the terms used, the specific meanings of some terms in this application are given below. When the following definition and the conventional meaning of a term conflict, the following definition shall prevail.

As used herein, "functional gene" means a gene that can exert its function in a host organism. For example, if the gene encodes one or more enzymes, then the host organism is capable of expressing said one or more enzymes, capable of being detected the activities of said one or more enzymes, and the functions of the enzymes are implemented in the host organism. Accordingly, the "gene having functionality" means that a host organism contains the gene and the gene plays its function in the host organism. Under such circumstances, the host organism can only contain the necessary part of the functional gene, as long as the necessary part enables the host organism to express the function of the functional gene.

As used herein, "gene inactivation or decreased activity" means that, compared to the reference that is without specific treatment, the gene underwent specific treatment loses its function or the function thereof is decreased, i.e. the activity of the gene can not be expressed in the host organism, or the expressed activity of the gene is decreased. This inactivation or decreased activity can be caused by a number of reasons. For example, gene inactivation or decreased activity may be due to gene deletion, gene mutation, antisense inhibition, gene silencing, the addition of an inhibitor, etc.

As used herein, "avermectin or analogues thereof" refers to avermectin or insect-resistant macrolide compounds having similar structures. They include, but are not limited to, avermectins, ivermectin, milbemycin, tenvermectins, etc.

Specifically, avermectin or analogues thereof can be avermectins B1a and B1b, tenvermectin, or tenvermectin A and B.

Avermectin and ivermectin are excellent pesticides and veterinary drugs, which have got a wide range of use in the last three decades. Ivermectin is obtained from structural modification of avermectin. But after nearly three decades of use, it will be phased out in the near future because of drug resistance problems. Therefore, corresponding alternative products are needed. Milbemycin belongs to a new generation of insect-resistant compounds produced from the fermentation of *Streptomyces hygroscopicus*. The insect-resistant activity of milbemycin is stronger than those of avermectins and ivermectin, but the toxicity of milbemycin is greatly lower than both of them. Taking the structures of avermectins B1a and B1b and the corresponding ivermectin and milbemycin as an example, the structural difference between milbemycin, avermectins and ivermectin is very small, and only lies in the three locations, as follows:

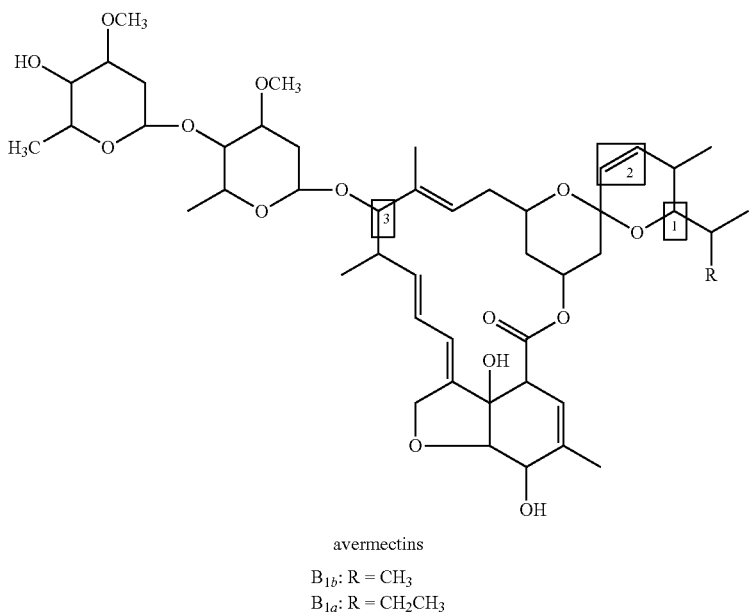

avermectins $B_{1b}$: R = $CH_3$
$B_{1a}$: R = $CH_2CH_3$

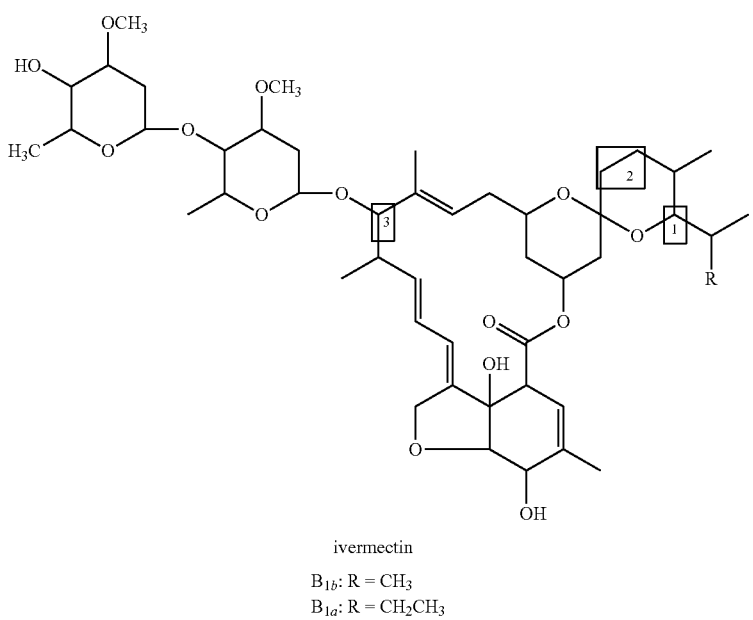

ivermectin $B_{1b}$: R = $CH_3$
$B_{1a}$: R = $CH_2CH_3$

-continued

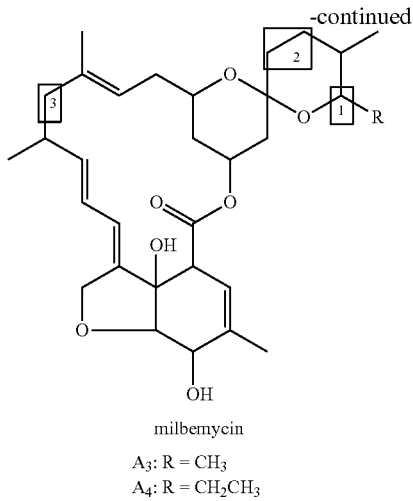

milbemycin

A₃: R = CH₃
A₄: R = CH₂CH₃

Thus, the difference between ivermectin and avermectins only lies in a single bond and a double bond at C22-23 positions (shown by 2 in structural formulae), but the insect-resistant activity of ivermectin is higher than those of avermectins. The structural differences between milbemycin and avermectins lie in the group at C25 position (shown by 1 in structural formulae), C22-23 positions and C13 position (shown by 3 in structural formulae). As described above, since milbemycin has superiority with respect to avermectins, it is considered that the structure of avermectins can be subjected to modification to make it closer to milbemycin, while retain some of its features, such as the disaccharide at C13 position, so that the activity and toxicity of avermectins can be improved.

Specifically, the carbohydrate derivative of 13-hydroxyl milbemycin having the following structure can be obtained by attaching a disaccharide structure to the C13 position of the macrolide ring of milbemycin:

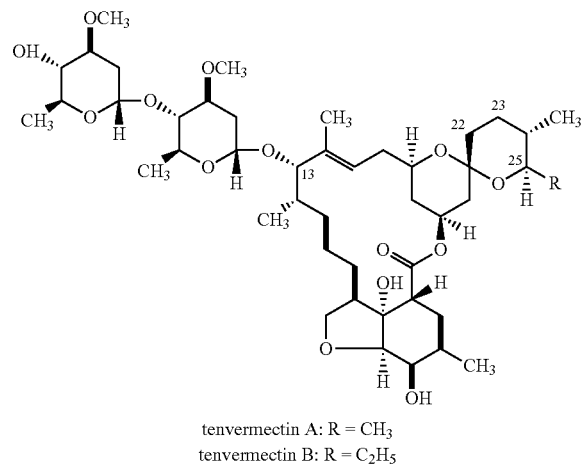

tenvermectin A: R = CH₃
tenvermectin B: R = C₂H₅

In the present disclosure, this carbohydrate derivative is called tenvermectin, and its two components are called tenvermectins A and B, respectively.

Through extensive research efforts, the inventors have found that, in the *Streptomyces* genome, replacement of the corresponding portion in the biosynthetic pathway of avermectins (i.e. aveAI gene) with milAI gene responsible for the structures of C22-C25 positions in the biosynthesis pathway of milbemycin can yield the avermectin analogues desired by the present invention (i.e. tenvermectin, including tenvermectins A and B).

Without being bounded by any theory, the inventors believe that the technical solutions of the present invention have designed a new biosynthetic pathway, which conjunctively uses both of the biosynthetic pathway of avermectins and the biosynthetic pathway of milbemycin; through replacing aveAI gene responsible for the synthesis of the structures at C22-C25 positions on the macrolide ring in the biosynthesis of avermectins in the avermectins-producing strain with milAI gene responsible for the synthesis of corresponding positions in the biosynthetic pathway of milbemycin, the avermectin analogues of the present invention (i.e. tenvermectin) are obtained completely by biosynthetic route.

Both of avermectins and milbemycin belong to macrolide compound, and the main structures thereof are both generated by polyketide synthase pathway (PKS pathway) in vivo. These two have similar main structures, and the PKS structures thereof are similar, too. For example, the construction of C22-25 positions of avermectins is determined by aveAI gene (GenBank: AB032367.1) including a loading area (LD), module 1 (SU1) and module 2 (SU2). The loading area is responsible for the group structure of C25 position, module 1 is responsible for the structures of C23-24 positions, module 2 is responsible for the reduction degree of C23 position. Correspondingly, the structures of C22-25 positions of milbemycin is determined by milAI gene (GenBank: NC_016582.1 (1146684 . . . 1159715)) including a loading area (LD), module 1 (SU1) and module 2 (SU2).

However, in the specific design of new biosynthetic pathways, in order to achieve gene replacement, a recombinant plasmid for gene replacement needs to be constructed. Because the size of the aveAI gene to be replaced is about 12 kb, the size of the milAI gene for replacement is about 13 kb. It is difficult for using such a large fragment to complete the construction of recombinant plasmid by conventional means such as enzyme digestion, PCR, etc.: as the fragment is too large, it is difficult to find a suitable operable single restriction site; and the use of PCR to amplify such a large fragment is characterized by low amplification efficiency on the one hand and the high likelihood of introducing mutation on the other hand. The inventors have found that such a large fragment replacement can be implemented by using intracellular gene recombination technology, and meanwhile, the milAI gene after replacement is able to function normally.

In addition, avermectins have two classes of components, i.e. A and B, the activity of component B is higher than that of component A. This is because the C5 position of component B is a hydroxyl group, whereas the C5 position of component A is oxymethyl. It is desired to obtain avermectins with decreased amount of component A or substantially free of component A. For example, the resulting avermectins are mainly composed from avermectins B1a and B1b.

Through extensive research efforts, the inventors have found that by inactivating aveD gene in avermectins-producing strain or decreasing the activity thereof, the yield of avermectin component A can be significantly reduced, or even substantially no avermectin component A is produced. Without being bounded by any theory, the inventors believe that this is because C5-oxymethyl transferase encoded by aveD gene (GenRank: AB032524.1) is capable of transferring methyl to C5-hydroxyl of component B so as to convert avermectin component B to component A. By inactivating aveD gene or significantly reduce the activity thereof, this metabolic process can be suppressed or even inactivated, thereby suppressing the generation of avermectin component A, and accordingly obtaining avermectin fermentation product mainly composed of avermectin component B (B1a and B1b). Accordingly, the present invention provides a technical solution, wherein the generation of component A is blocked by inactivating aveD gene, thereby further enhancing the activity of avermectins and reducing the toxicity thereof.

Example 1 Construction of Recombinant
*Streptomyces avermitilis* Strain MA220

1. Extraction of genomic DNA of *Streptomyces avermitilis* and *Streptomyces hygroscopicus*:
   a) The spores of *Streptomyces avermitilis* MA-4680 (*Streptomyces avermitilis* MA-4680. ATCC No. 31267) and *Streptomyces hygroscopicus* HS023 (*Streptomyces hygroscopicus* HS023. CGMCC No. 7677) were respectively inoculated into 30 ml TSB medium (Tryptic Soy Broth, BD Company, article number 211822), 30° C., 220 rpm, cultured for 30-48 h.
   b) Mycelia were collected by centrifugation. After washed with sterile water for twice, the mycelia were suspended in lysozyme solution (10.3% sucrose, 10 mM Tris-HCl, pH8.0, 4 mg/ml lysozyme) at 4 times the amount of mycelia volume, and incubated in 37° C. water bath for 1-2 h.
   c) 1/10 volume of 10% SDS solution was added, and 20 mg/ml of proteinase K solution was added till a final concentration of 100 µg/ml, and incubated in 37° C. water bath for 30 min-1 h.
   d) an equal volume of phenol-chloroform solution (phenol:chloroform:isoamyl alcohol=25:24:1, pH8.0) was added, and extracted for twice.
   e) 1/10 volume of 3 M NaAc-HAc solution (pH5.3) and an equal volume of isoamyl alcohol was added to the supernatant, centrifuged at 12000 rpm for 5 min to precipitate genomic DNA.
   f) The precipitate was washed with 70% ethanol for twice, and after drying at room temperature, was dissolved with 10 mM Tris-HCl solution (pH8.0) containing 20 µg/ml RNase to obtain the genomic DNA solution.

Figure 2:
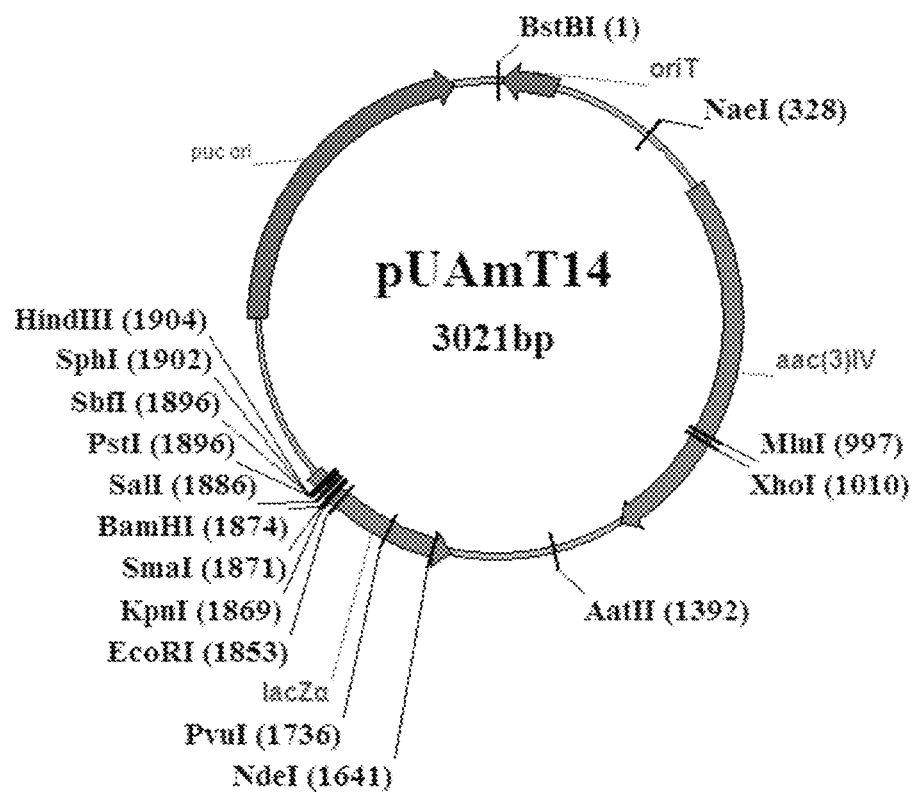
FIG. 2: The physical map of recombinant plasmid pUAmT14.

2. Construction of vector pUAmT14:
   Plasmid pIJ773 (obtained from Plant Bioscience Limited, Norwich, UK; see Gust B, et al., PCR-targeted *Streptomyces* gene replacement identifies a protein domain needed for biosynthesis of the sesquiterpene soil odor geosmin. (2003) Proc Natl Acad Sci USA 100 (4): 1541-1546; and Gust B, et al., REDIRECT Technology: PCR-targeting system in *streptomyces coelicolor*. Norwich: John Innes Centre. (2002)) was subjected to double restriction digestion with XbaI (TaKaRa) and BstBI (TaKaRa) according to the instructions. The fragment of 1271 bp containing aac(3)IV gene and oriT was recovered by electrophoresis, and blunted with BKL kit (TaKaRa) according to the instructions to obtain fragment 1. The pUC19 vector was subjected to double restriction digestion with DraI (TaKaRa) and SspI (TaKaRa) according to the instructions. The vector fragment of 1748 bp was recovered by electrophoresis to obtain fragment 2. The fragments 1 and 2 were ligated (with the Solution I solution of TaKaRa company according to the instructions, the same below) to obtain recombinant plasmid pUAmT14. The physical map of pUAmT14 is shown in FIG. 2.

3. Construction of recombinant plasmid pUAmT-kaveD for inactivating aveD gene of *Streptomyces avermitilis*:
   The DNA fragment present on Cosmid 6-9 (see Reference 4: Haiyang Xia, Jun Huang, Minjie Hu, etc., Construction of and ordered cosmid library of *S. avermitilis* for genetic modification of the industrial strains, Chinese Journal of Antibiotics, 2009, 34 (7): 403-405) is the base position no. 1124992-1167304 of the *Streptomyces avermitilis* MA-4680 genome. The fragment at positions 442-521 of aveD gene (SEQ ID NO: 1) was knocked out by means of PCR targeting technology. By removing resistance gene cassette by means of the FLP recombinase, recombinant plasmid 6-9kaveD was obtained with the 81 bp sequence being replaced by new one (SEQ ID NO: 2). The PCR targeting was implemented essentially according to the method disclosed in literature (see Gust B, et al., PCR-targeted *Streptomyces* gene replacement identifies a protein domain needed for biosynthesis of the sesquiterpene soil odor geosmin. (2003) *Proc Natl Acad Sci USA* 100 (4): 1541-1546; and Gust B, et al., REDIRECT Technology: PCR-targeting system in *streptomyces coelicolor*. Norwich: John Innes Centre. (2002)). The Specific procedure is as follows:
   a) Design of PCR primer: The primer aveD59 (SEQ ID NO: 3) was designed, wherein the 39 bp at 5'-end is the same as the bases at positions 403-441 of aveD gene, and the 20 bp at 3'-end is the "left arm" of template resistance gene cassette; the primer aveD58 (SEQ ID NO: 4) was designed, wherein the 39 bp at 5'-end is in reverse complementation with the bases at positions 522-560 of aveD gene, and the 20 bp at 3'-end is the "right arm" of template resistance gene cassette ("left arm" and "right arm" are fixed sequence, see Gust B, Kiser T, Chater K F. REDIRECT Technology: PCR-targeting system in *streptomyces coelicolor*. Norwich: John Innes Centre. 2002, p. 6).
   b) PCR amplification of resistance gene cassette: PCR amplification was implemented using plasmid pIJ773 as the template, wherein the PCR used PrimeSTAR DNA polymerase from TaKaRa company.

The following reaction solutions were formulated:

| | |
|---|---|
| The primer aveD59 (25 µM) | 0.5 µl |
| The primer aveD58 (25 µM) | 0.5 µl |
| Plasmid pIJ773 | 0.2 µl (about 10 ng) |
| 5× PrimeSTAR buffer | 10 µl |
| dNTPs (each of 2.5 mM) | 4 µl |

-continued

| PrimeSTAR DNA polymerase (2.5 U/μl) | 0.5 μl |
| Double distilled water | 34 μl |

PCR Reaction Procedure:
94° C., 2 min,
(98° C.×10 sec, 50° C.×45 sec, 72° C.×1 min 30 sec)×10 cycles,
(98° C.×10 sec, 68° C.×1 min 30 sec)×15 cycles,
72° C.×2 min, 16° C.×1 min.

The PCR product was subjected to agarose gel electrophoresis. The gel was cut and the target fragment of about 1.4 kb was recovered. The recovery was implemented with a gel recovery kit (TaKaRa) according to the instructions.

c) Transforming the library plasmid into *E. coli* BW25113/pIJ790: A single colony of *E. coli* BW25113/pIJ790 was inoculated into 10 ml of LB culture medium containing 25 μg/ml chloramphenicol (tryptone 1.0%, yeast powder 0.5%, NaCl 0.5%, glucose 0.1%), and cultured at 30° C., 250 rpm shaking overnight (14-18 h, the same below). 100 μl of overnight bacterial fluid was transferred to 10 ml SOB medium containing 25 μg/ml chloramphenicol (tryptone 2.0%, yeast powder 0.5%, NaCl 0.05%, 10 ml of 250 mmol/L KCl solution was added per liter, and 5 ml of sterile 2 mol/L $MgCl_2$ was added per liter prior to use), cultured at 30° C., 250 rpm for 3-4 h, till an $OD_{600}$ of about 0.4. At 4° C., centrifugation was implemented at 4000 rpm for 5 min to collect the bacterial cells. The bacterial cells were washed with 10 ml of ice-cold 10% glycerol for twice, suspended with 100 μl of ice-cold 10% glycerol, i.e. turned into electrotransformation competent cells. To 50 μl of competent cells was added approximately 100 ng (2-3 μl) library plasmid cosmid6-9, and electrotransformation was implemented in a 0.2 cm ice-cold electric shock cup. The electric shock parameters were: 200, 25 g, 2.5 kV. The electric shock duration was between 4.5-4.9 ms. After electric shock, 1 ml of ice-cold LB medium was added immediately, and cultured at 30° C. with shaking for 1 h. 50 μl of transformation solution was spread onto LB plates (LB culture medium containing 1.5% agar powder) containing 100 m/ml carbenicillin, 50 μg/ml kanamycin and 25 μg/ml chloramphenicol, cultured at 30° C. overnight, so that single colonies were grown out.

d) PCR targeting of library plasmid: An *E. coli* BW25113/pIJ790 single colony containing library plasmid cosmid6-9 was randomly picked out and was inoculated into 10 ml of LB medium containing 100 μg/ml carbenicillin, 50 μg/ml kanamycin and 25 μg/ml chloramphenicol, cultured at 30° C. with 250 rpm shaking overnight. 100 μl of overnight bacterial culture was transferred to 10 ml of SOB medium containing 100 m/ml carbenicillin, 50 μg/mlkanamycin, 25 μg/ml chloramphenicol and 10 mM L-arabinose, cultured at 30° C. with 250 rpm shaking. Electrotransformation competent cells were prepared according to the method in step c). To 50 μl of competent cells was added approximately 100 ng (2-3 μl) of the recovered solution of PCR product obtained in step b), and electric shock was implemented in a 0.2 cm ice-cold electric shock cup. The electric shock parameters were: 200Ω, 25 μF, 2.5 kV. The electric shock duration was between 4.5-4.9 ms. One milliliter of ice-cold LB medium was added immediately, and the ells were cultured at 37° C. with shaking for 1 h. After brief centrifugation, most of the supernatant was removed, the precipitate was suspended with the remaining supernatant and spread onto LB plates containing 100 μm/ml carbenicillin, 50 μg/ml kanamycin and 50 μg/ml apramycin, cultured at 37° C. overnight. A single colony was picked out and suspended in 3 ml of LB medium containing 100 μg/ml carbenicillin, 50 μg/ml kanamycin and 50 μg/ml apramycin, cultured at 37° C. with 250 rpm shaking for around 6 h. The plasmid was extracted with Axygen Plasmid DNA Purification Miniprep Kit according to the instructions, and subjected to restriction digestion test to screen the correct plasmid. Recombinant plasmid 6-9daveD was obtained.

e) Removing the resistance gene and oriT by FLP: *E. coli* DH5α/BT340 was inoculated into 10 ml of LB medium containing 25 μg/ml chloramphenicol, cultured at 30° C. with 250 rpm shaking overnight. Electrotransformation competence was prepared according to the method in step c). To 50 μl of competent cells was added approximately 100 ng (2-3 μl) of the recombinant plasmid 6-9daveD obtained in step d), and electric shock was implemented in a 0.2 cm ice-cold electric shock cup. The electric shock parameters were: 200Ω, 25 μF, 2.5 kV. The electric shock duration was between 4.5-4.9 ms. One milliliter of ice-cold LB medium was added immediately, and the cells were cultured at 30° C. with shaking for 1 h. 50 μl of transformation solution was coated onto LB plates containing 50 μg/ml apramycin and 25 μg/ml chloramphenicol, cultured at 30° C. for 48 h. Single colonies were grown out. A single colony was randomly picked out and isolated on a LB plate without antibiotics by streaking, cultured at 42° C. overnight, such that it expressed FLP recombinase and lost plasmid BT340 subsequently. 20-30 single colonies were picked out and respectively streaked on LB plates containing 50 μg/ml apramycin and LB plates containing 50 μg/ml kanamycin, cultured at 37° C. overnight. Clones that are apramycin-sensitive and kanamycin-insensitive are target clones wherein resistance gene cassette was removed. Target clones were picked out for extraction of plasmids, and the plasmids were subjected to restriction digestion to screen the correct plasmid. Recombinant plasmid 6-9daveD was obtained.

Figure 3:
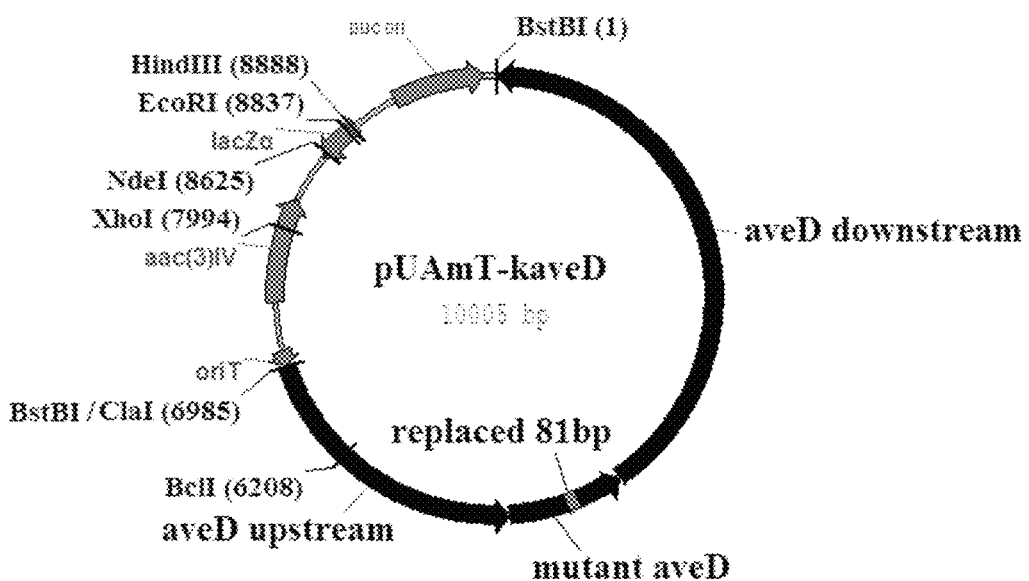
FIG. 3: The physical map of recombinant plasmid pUAmT-kaveD.

Construction of recombinant plasmid pUAmT-kaveD: the recombinant plasmid 6-9kaveD was subjected to double enzyme digestion with ClaI (TaKaRa) and BstBI (TaKaRa) according to the instructions to recover a fragment of 6984 bp, which was ligated to vector pUAmT14 that was subjected to enzymatic digestion by BstBI and dephosphorylation (i.e. to the digestion reaction solution was directly added 1 μl of FastAP (Fermentas), cultured at 37° C. in water bath for 5-10 min, the same below) to yield recombinant plasmid pUAmT-kaveD. The physical map thereof is shown in FIG. 3.

4. Inactivation of *Streptomyces avermitilis* MA-4680 aveD gene:

a) Transferring the recombinant plasmid pUAmT-kaveD into *Streptomyces avermitilis* MA-4680 with intergeneric conjugation: *E. coli* ET12567 (pUZ8002) was prepared into the electrotransformation competent cells according to the method described in Step 3-c) (culture temperature was 37° C., final concentration of antibiotics in culture medium: chloramphenicol 25 μg/ml, kanamycin 25 μg/ml): to 50 μl competent cells was added about 100 ng (1-2 μl) recombinant plasmid pUAmT-kaveD, and electrotransformation was implemented in a 0.2 cm ice-cold electrical shock cup. The electric shock parameters were: 200Ω, 25 μF, 2.5 kV. After the electrical shock was completed, 1 ml of ice-cold LB culture medium was added immediately, and the cells were cultured at 37° C. with shaking for 1 h. 50 μl of transformation solution was spread onto LB plates containing 50 μg/ml apramycin, 100 μg/ml carbenicillin, 50 μg/ml kanamycin and 25 μg/ml chloramphenicol, cultured at 37°

Figure 4:
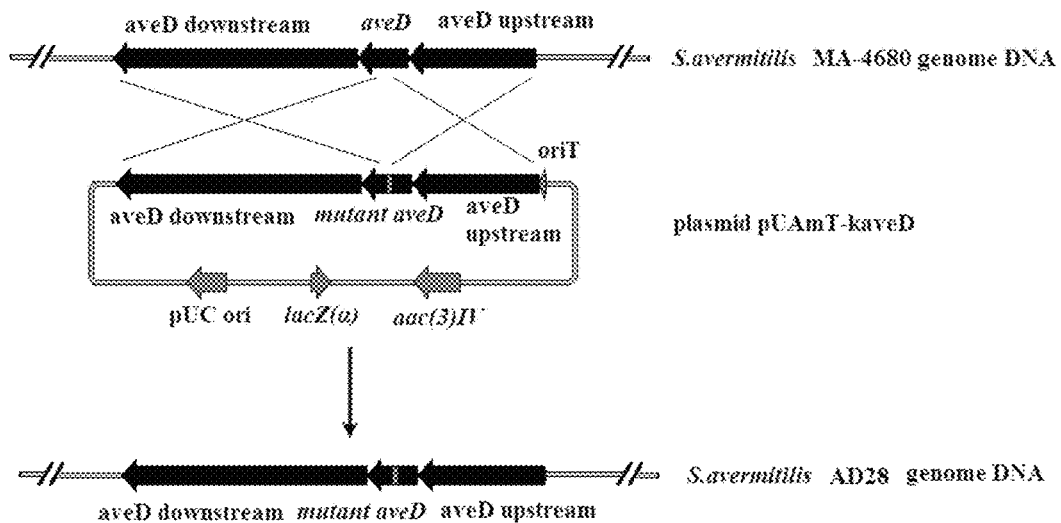
FIG. 4: The schematic diagram of inactivation process of aveD gene of the original strain *Streptomyces avermitilis* MA-4680.

C. overnight. A transformant was randomly selected and inoculated to 10 ml of LB culture medium containing 25 μg/ml chloramphenicol, 100 μg/ml carbenicillin, 50 μg/ml kanamycin and 50 μg/ml apramycin, cultured at 37° C. with 250 rpm shaking overnight. 100 μl of overnight bacterial culture was transferred to 10 ml of fresh LB culture medium containing 25 μg/ml chloramphenicol, 50 μg/ml kanamycin and 50 μg/ml apramycin, cultured at 37° C. with 250 rpm till an $OD_{600}$ of around 0.4. The cells was washed twice with 10 ml of LB medium, and suspended in 1 ml of LB. 500 μl of bacterial culture was mixed with about $10^8$ cells of *Streptomyces avermitilis* MA-4680 spores which were previously suspended in 500 μl 2×YT medium (tryptone 1.6%, yeast powder 1.0%, NaCl 0.5%) and treated by 50° C. heat shock for 10 min. After brief centrifugation, most of the supernatant was discarded, and the cells were suspended with the remaining supernatant, and spread onto the MS plates (soybean meal 2%, mannitol 2%, agar powder 2%) containing 10 mM $MgCl_2$, cultured at 30° C. for 16-20 h. Sterile water containing 0.5 mg nalidixic acid and 1.25 mg apramycin was spread onto the plates, cultured continuously at 30° C. for about 5 d to grow the transformants.

b) Screening of inactivated aveD gene mutant: after passaged once at YMS (yeast extract 0.4%, soluble starch 0.4%, malt extract 1.0%, agar powder 1.8%) plates containing 20 μg/ml nalidixic acid and 25 μg/ml apramycin, transformants were further passaged twice at YMS plates without antibiotics, so that single colonies were isolated. Single colonies were respectively cultured on YMS medium containing 25 μg/ml apramycin and antibiotic-free YMS culture medium to screen apramycin-selective strains. The screened apramycin-selective strains were subjected to genomic DNA extraction according to the method of step 1 of the present Example. PCR test was performed with rTaq DNA polymerase (TaKaRa, the same below) according to the instructions using primers aveDF (SEQ ID NO: 5)/aveDR (SEQ ID NO: 6) and aveDF (SEQ ID NO: 5)/aveDM (SEQ ID NO: 7). The target strains are: 1094 bp can be amplified with the former, whereas the target strip can not be amplified with the latter. The No. AD28 strain obtained after screening was regarded as the target strain for carrying out further genetic modification thereon. The inactivation process of aveD gene of the original strain *Streptomyces avermitilis* MA-4680 is shown by FIG. 4.

Figure 5:
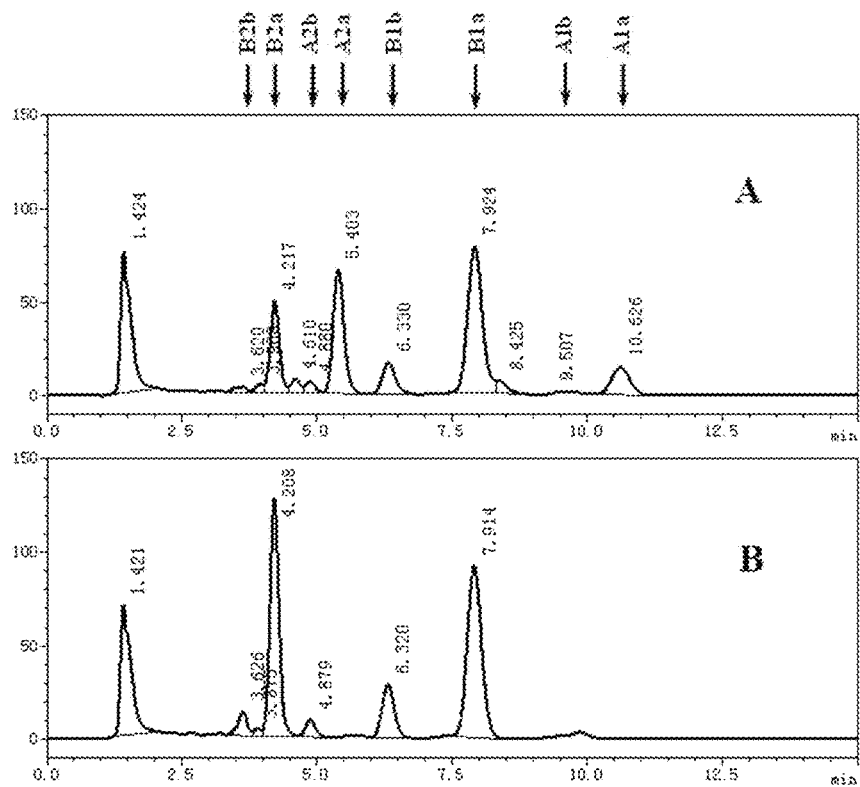
FIG. 5: The HPLC chromatogram of the fermentation broth. A is the chromatogram of the fermentation broth of the original strain MA-4680, B is the chromatogram of the fermentation broth of genetically engineered strain AD28.

5. Fermentation validation of genetically engineered strain AD28: A single colony of AD28 was inoculated into a seed medium (corn starch 2.5%, soybean meal 0.8%, peanut meal 1%, yeast powder 0.95%, $CoCl_2$ 0.003%, pH7.2-7.4), cultured at 28° C., 250 rpm for 40 h, and was transferred to fermentation medium (corn starch 14%, amylase 0.003%, soybean meal 2.0%, yeast powder 1%, zeolite powder 0.2%, $MnSO_4$ 0.0024%, $Na_2MoO_4$ 0.0024%, $CoCl_2.6H_2O$ 0.002%, pH7.2-7.4) at an inoculation amount of 6%, cultured at 28° C., 250 rpm for 8 d. One milliliter of fermentation broth was added to 4 ml of anhydrous methanol for soaking, ultrasonically treated for 1 h, and filtered. The filtrate was used directly for HPLC analysis. Conditions for HPLC analysis were: chromatographic column: C18 Hypersil ODS2 4.6×250×5 (Dalian Elite); mobile phase: methanol:ethanol:water=81:7:12; flow rate: 1 ml/min; absorption wavelength: 240 nm. Results are shown in FIG. 5: A is the HPLC chromatogram of the fermentation broth of the original strain MA-4680, B is the HPLC chromatogram of the fermentation broth of genetically engineered strain AD28. The results show that the genetically engineered strain AD28 no longer produces avermectin component A by fermentation.

Figure 6:
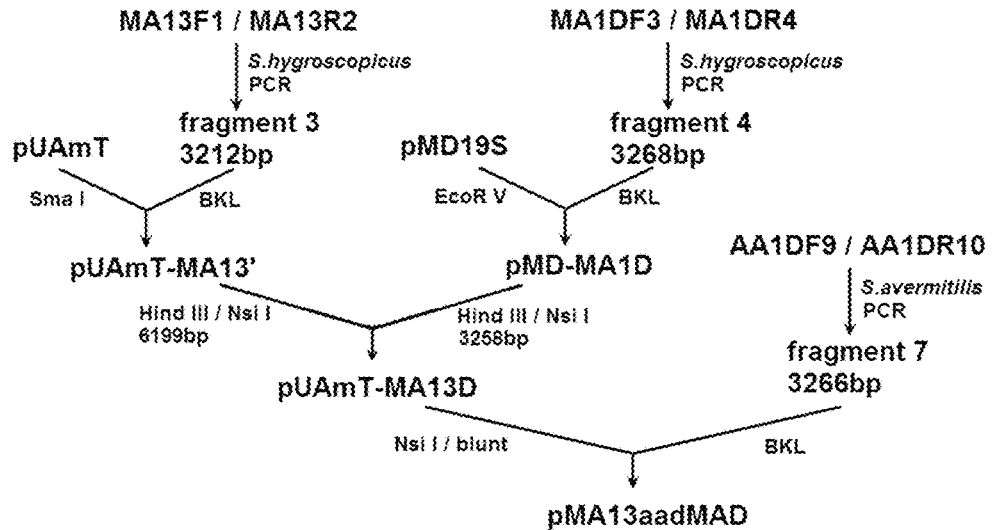
FIG. 6: The flowchart of construction of recombinant plasmid pMA13aadMAD.

6. Construction of recombinant plasmid pMA13aadMAD for replacement of downstream fragment of milAI gene of *Streptomyces hygroscopicus*: Taking genomic DNA of *Streptomyces hygroscopicus* HS023 as template, PCR reaction was performed with PrimeSTAR DNA polymerase (TaKaRa, the same below) according to the instructions by using primers MA13F1 (SEQ ID NO: 8) and MA13R2 (SEQ ID NO: 9). The target fragment 3 of 3212 bp was obtained. The recombinant plasmid pUAmT14 was subjected to enzymatic digestion with SmaI, then dephosphorylated with FastAP, and ligated with fragment 3 which was previously treated by BKL kit, so that recombinant plasmid pUAmT-MA13' was obtained. Taking *Streptomyces hygroscopicus* genomic DNA as template, using primers MA1DF3 (SEQ ID NO: 10) and MA1DR4 (SEQ ID NO: 11), PCR reaction was implemented by PrimeSTAR DNA polymerase to yield fragment 4 of 3268 bp. Recombinant plasmid pUAmT-MA13' was subjected to restriction digestion with EcoRV (TaKaRa), then underwent dephosphorylation with FastAP, ligated with fragment 4 previously treated by BKL kit, resulting in recombinant plasmid pMD-MA1D. The recombinant plasmid pUAmT-MA13' was subjected to double enzymatic digestion with HindIII+NsiI according to the instructions (TaKaRa), and the gel was cut to recover a fragment of 6199 bp, i.e. fragment 5; recombinant plasmid pMD-MA1D was subjected to double enzymatic digestion with HindIII+NsiI, and the gel was cut to recover a fragment of 3258 bp, i.e. fragment 6. Fragments 5 and 6 were ligated to obtain recombinant plasmid pUAmT-MA13D. Taking genomic DNA of *Streptomyces avermitilis* MA-4680 as template, PCR reaction was performed with PrimeSTAR DNA polymerase by using primers AA1DF9 (SEQ ID NO: 12) and AA1DR10 (SEQ ID NO: 13), resulting in fragment 7. Recombinant plasmid PUAmT-MA13D was subjected to restriction digestion with NsiI (TaKaRa) according to the instructions and then recovered, and treated with BKL kit; the reaction product was dephosphorylated with FastAP, and then ligated with fragment 7 treated by BKL kit to yield the recombinant plasmid pMA13aadMAD for replacement of downstream fragment of milAI gene of *Streptomyces hygroscopicus*. The construction procedure is shown in FIG. 6.

Figure 7:
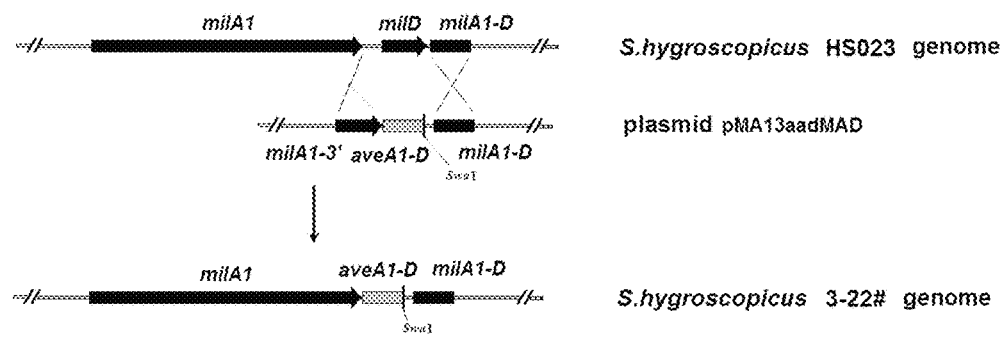
FIG. 7: The schematic diagram of genome variation from the original strain *Streptomyces hygroscopicus* HS023 to the #3-22 strain.

7. Replacement of downstream fragment of milAI gene of *Streptomyces hygroscopicus*: The recombinant plasmid pMA13aadMAD was transformed into *Streptomyces hygroscopicus* HS023 according to the conjugal transfer method described in step 4-a). Transformants were underwent two antibiotics-free screening and passaged, then single colonies were picked out by toothpicks, respectively cultured on YMS plates containing 25 μg/ml apramycin and YMS plates without antibiotics at 28° C. for 5-6 d. Single colonies that did not grow on YMS culture medium containing apramycin but grew on YMS culture medium without apramycin were selected to implement scale-up culture on YMS medium, and meanwhile, genomic DNA was extracted according to the method of Step 1, and PCR test was carried out with rTaq DNA polymerase using primers milDF11 (SEQ ID NO: 14) and milDR12 (SEQ ID NO: 15). The target strain is the one wherein the PCR product is 3825 bp, and the revertant strain is the one wherein the PCR product is 1467 bp. From the results of screening, 3-22 # strain was determined to be *Streptomyces hygroscopicus* whose downstream fragment of milAI gene was successfully replaced, which was regarded as the target strain to be further operated. The schematic diagram of genome variation from the original strain HS023 to the #3-22 strain is shown in FIG. 7.

Figure 8:
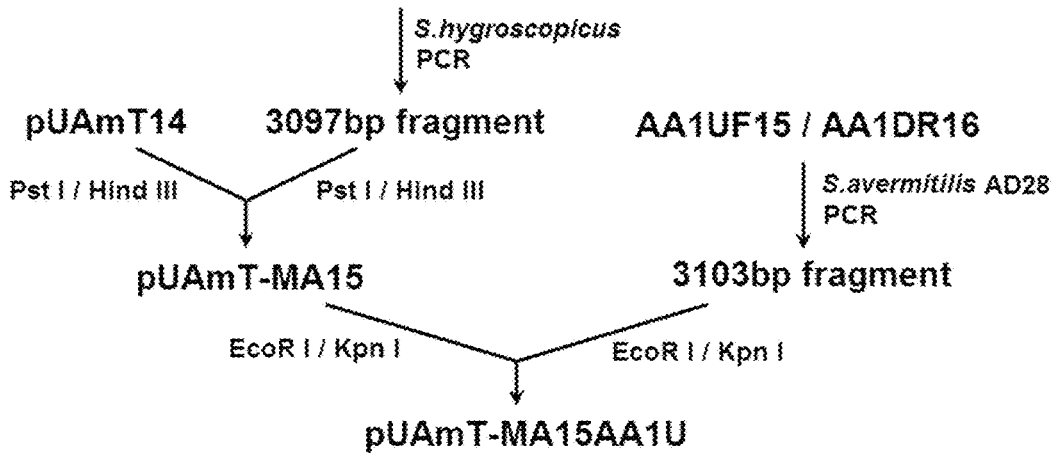
FIG. 8: The flowchart of construction of recombinant plasmid pUAmT-MA15AA1U.

8. Construction of recombinant plasmid pUAmT-MA15AA1U for inserting the upstream fragment of aveAI gene of *Streptomyces avermitilis* AD28 into milAI gene upstream of *Streptomyces hygroscopicus*: Taking *Streptomyces hygroscopicus* HS023 genomic DNA as template, PCR amplification was implemented with PrimeSTAR DNA polymerase using primers MA15F13 (SEQ ID NO: 16) and MA15R14 (SEQ ID NO: 17), resulting in a fragment of 3097 bp; the resulting fragment was underwent double enzymatic digestion with PstI and HindIII according to the instructions (TaKaRa), ligated with plasmid pUAmT14 underwent the same enzymatic digestion, resulting in the recombinant plasmid pUAmT-MA15. Taking genomic DNA of *Streptomyces avermitilis* AD28 (the method for extraction of genomic DNA is the same as step 1 of the present Example) as template, PCR amplification was implemented with PrimeSTAR DNA polymerase using primers AA1UF15 (SEQ ID NO: 18) and AA1DR16 (SEQ ID NO: 19), resulting in a fragment of 3103 bp; the resulting fragment was underwent double enzymatic digestion with EcoRI and KpnI according to the instructions (TaKaRa), ligated with the recombinant plasmid pUAmT-MA15 underwent the same enzymatic digestion, resulting in recombinant plasmid pUAmT-MA15AA1U. The construction procedure is shown in FIG. 8.

Figure 9:
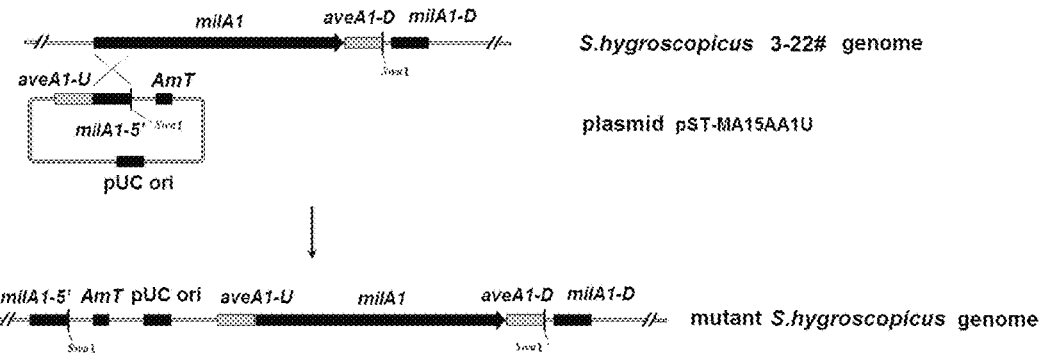
FIG. 9: The schematic diagram of inserting upstream fragment of aveAI gene into the genome of the #3-22 strain.

Insertion of the upstream fragment of aveAI gene of *Streptomyces avermitilis* into milAI gene upstream of *Streptomyces hygroscopicus*: According to the method described in step 4-a), the recombinant plasmid pUAmT-MA15AA1U obtained in step 8 was transformed into 3-22# strain obtained in step 7 by conjugation, and the transformant, i.e. the target strain was grown out. The schematic diagram of inserting upstream fragment of aveAI gene into the genome of the #3-22 strain is shown in FIG. 9.

Figure 10:
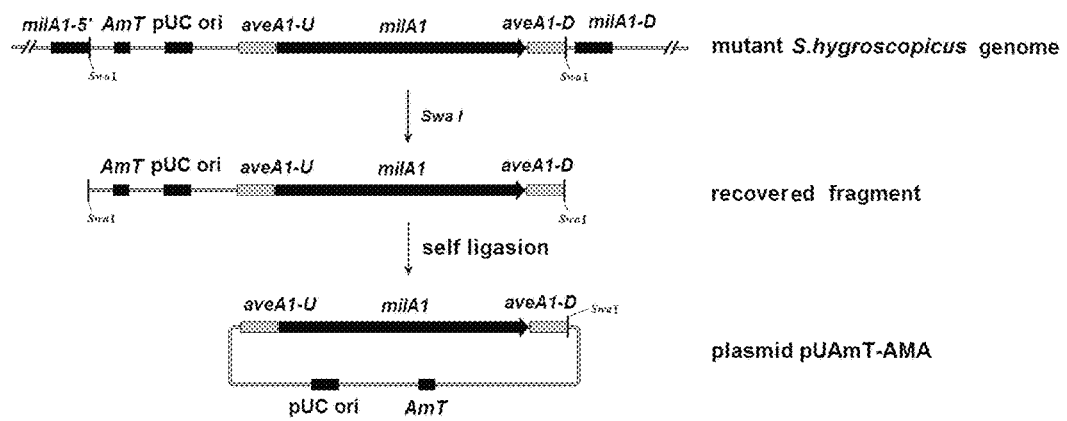
FIG. 10: The flowchart of construction of recombinant plasmid pUAmT-AMA.

10. Construction of the recombinant plasmid pUAmT-AMA for replacement of aveAI gene of *Streptomyces avermitilis* with milAI gene of *Streptomyces hygroscopicus*: A single colony was picked out from the transformants obtained in step 9, and was inoculated to TSB culture medium containing 20 μg/ml nalidixic acid and 25 μg/ml apramycin, and genomic DNA thereof was extracted by the method of step 1. The extracted genomic DNA was subjected to restriction digestion reaction with SwaI (TaKaRa) according to the instructions. After completion of the reaction, 1/10 volume of 3 M NaAc-HAc solution (pH5.3) and an equal volume of isoamyl alcohol were added, centrifugated at 12000 rpm for 5 min to precipitate DNA. The precipitate was washed twice with 70% ethanol; after dried at room temperature, it was dissolved with 20 μl of 10 mM Tirs-HCl solution (pH 8.0) to obtain the recovery fluid. Three microliter of recovery fluid was taken to transform *E. coli* DH5α competent cells (the preparation method and the electrotransformation process of DH5α competent cells were the same as those in step 3-c), but in the culture medium, no antibiotics was added, and the culture temperature was 37° C.). The transformation fluid was centrifuged to remove most of the supernatant, and the precipitate was suspended with the residual fluid, spread onto LB plates containing 25 μg/ml apramycin in whole amount, cultured for 16 h at 37° C., and transformants were grown out. The transformants were extracted for plasmid, i.e. the recombinant plasmid pUAmT-AMA for replacement of aveAI gene of *Streptomyces avermitilis* with milAI gene of *Streptomyces hygroscopicus*. The construction process of pUAmT-AMA is shown in FIG. 10.

Figure 11:
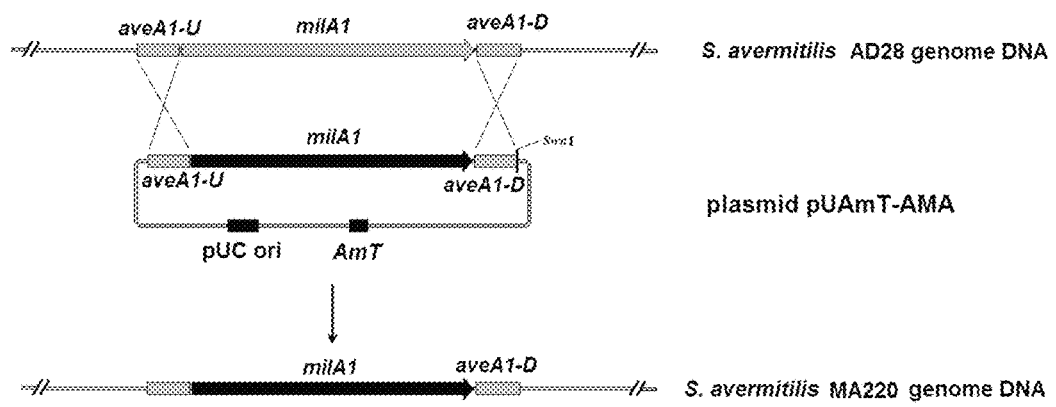
FIG. 11: The diagram of genome variation process from genetically engineered strain AD28 to MA220.

11. Replacement of aveAI gene of *Streptomyces avermitilis*: The recombinant plasmid pUAmT-AMA was transformed into AD28 strain obtained in step 4 according to the conjugation method described in step 4 a). Transformants were underwent two antibiotics-free screening and passaged, then single colonies were picked out by toothpicks, respectively cultured on YMS plates containing 25 μg/ml apramycin and YMS plates without antibiotics at 28° C. for 5-6 d. Single colonies that did not grow on YMS culture medium containing apramycin but grew on YMS culture medium without antibiotics were selected to implement scale-up culture on YMS medium, and meanwhile, genomic DNA was extracted according to the method of Step 1 of the present Example, and PCR test was carried out with rTaq DNA polymerase using primer pairs 025A1EF (SEQ ID NO: 20)/026A1ER (SEQ ID NO: 21) and 027M1EF (SEQ ID NO: 22)/028M1ER (SEQ ID NO: 23). Genetically engineered strain with successful replacement was the one wherein primer pair 025A1EF (SEQ ID NO: 20)/026A1ER (SEQ ID NO: 21) was capable of amplifying a target fragment of 2005 bp, whereas 027M1EF (SEQ ID NO: 22)/028M1ER (SEQ ID NO: 23) was not capable of obtaining target fragment. Genetically engineered strain MA220 with successful replacement was picked out as the target strain for carrying out the next experiment thereon. The genome variation process from genetically engineered strain AD28 to MA220 is shown in FIG. 11.

Figure 12:
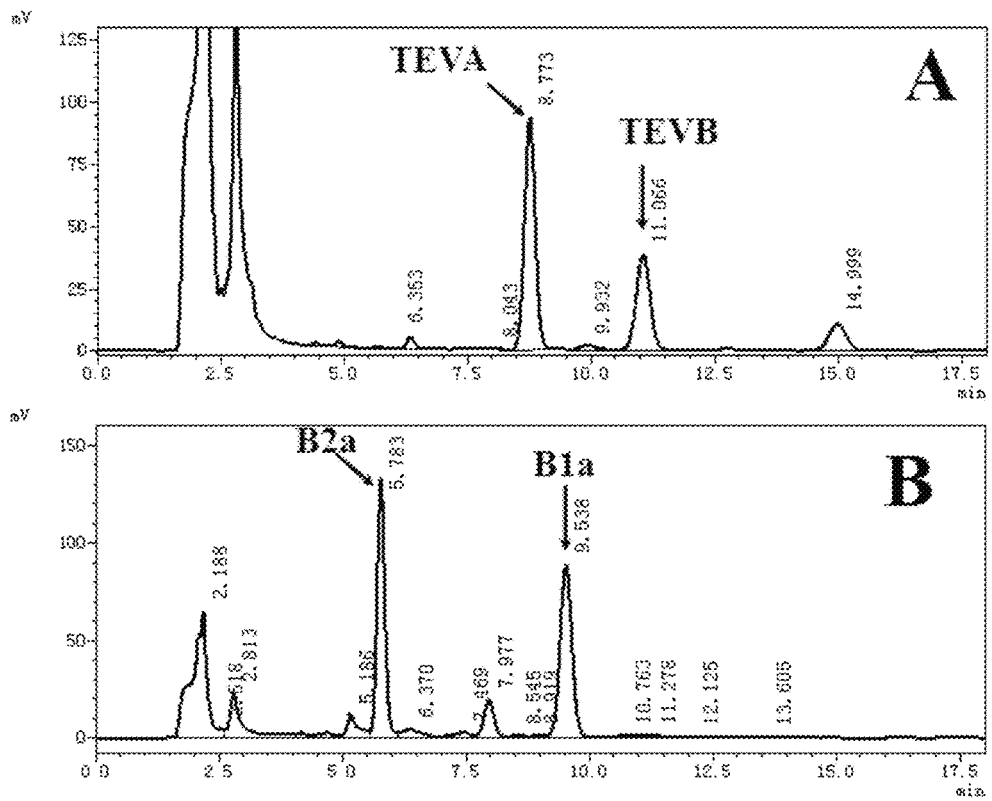
FIG. 12: Comparison between the fermentation products of the genetically engineered strain AD28 and MA220. A is the HPLC chromatogram of the fermentation sample of the genetically engineered strain MA220, B is the HPLC chromatogram of the fermentation sample of the genetically engineered strain AD28.
Figure 13:
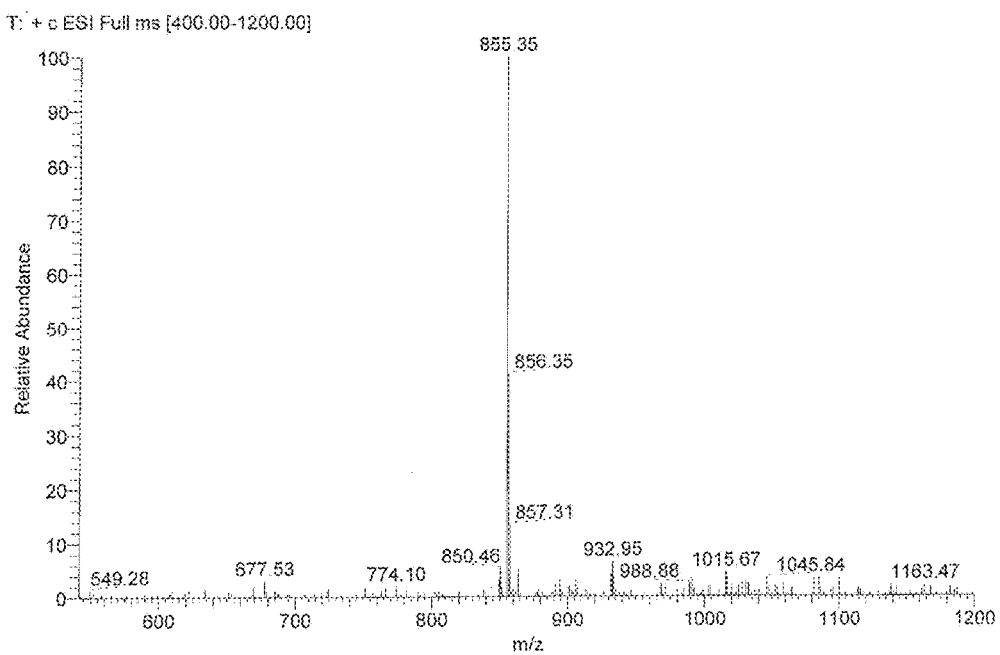
FIG. 13: The mass spectrum of tenvermectin A.
Figure 14:
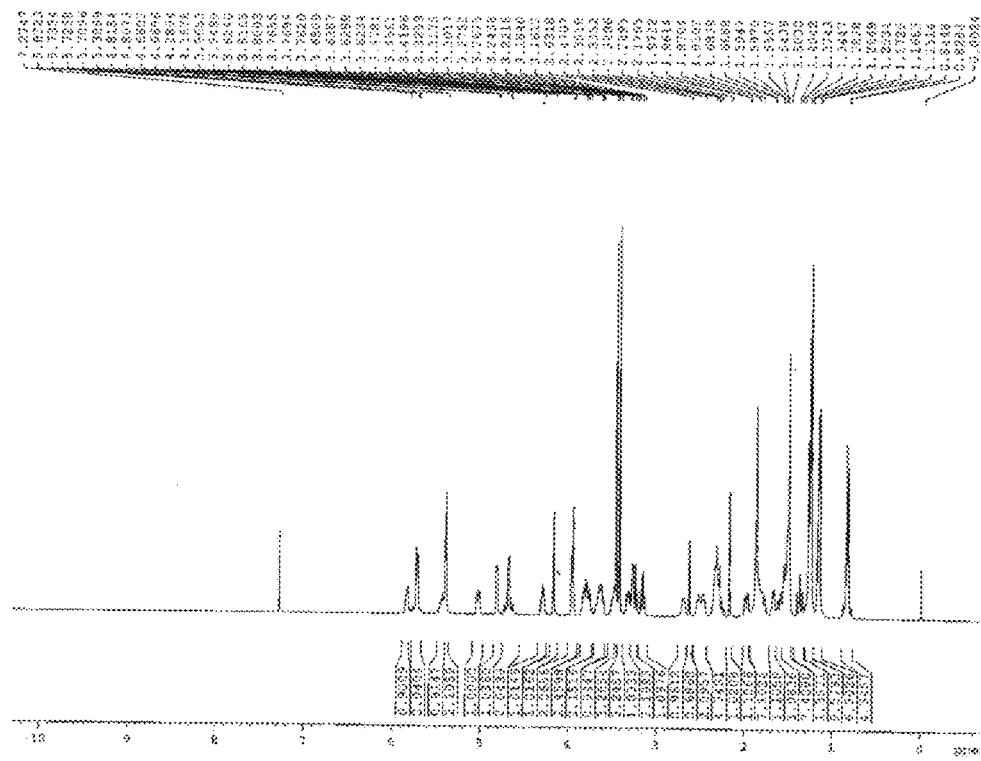
FIG. 14: The $^1$H-NMR spectrum of tenvermectin A dissolved in $CDCl_3$.
Figure 15:
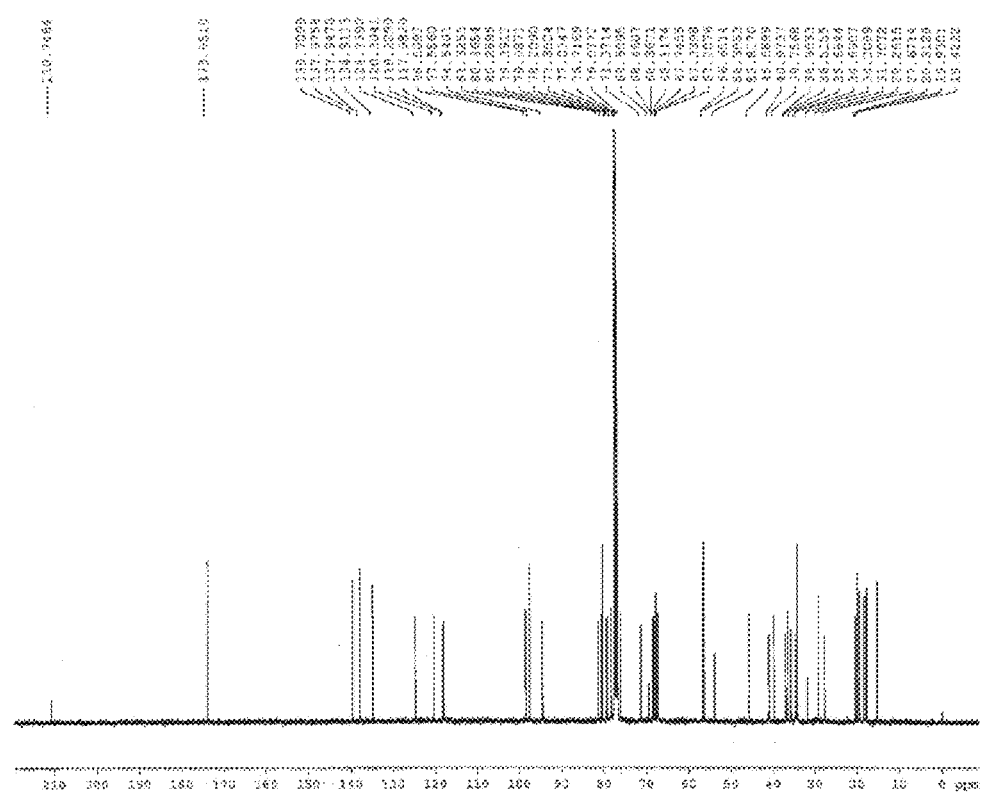
FIG. 15: The $^{13}$C-NMR spectrum of tenvermectin A dissolved in $CDCl_3$.
Figure 16:
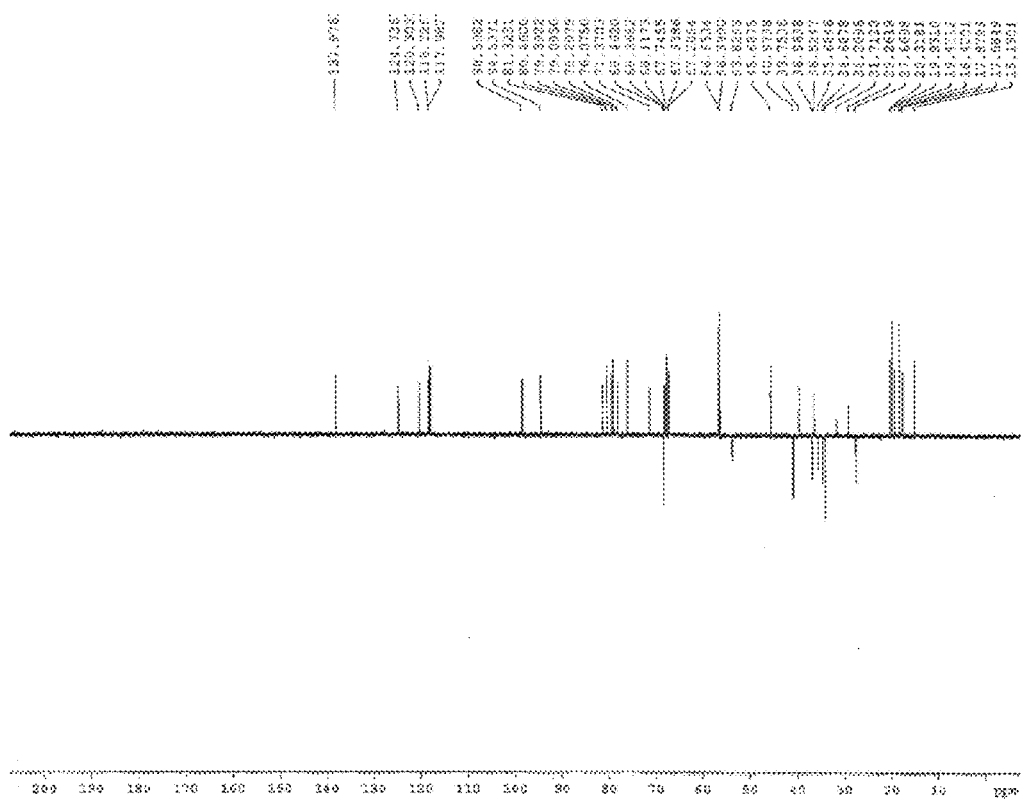
FIG. 16: The DEPT135 spectrum of tenvermectin A dissolved in $CDCl_3$.
Figure 17:
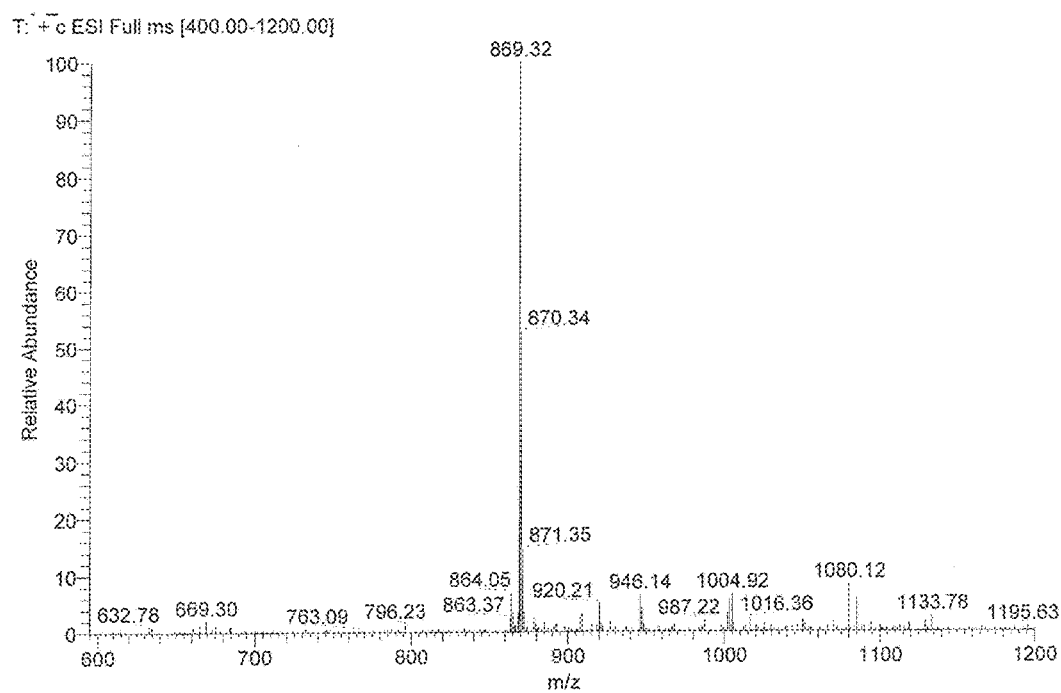
FIG. 17: The mass spectrum of tenvermectin B.
Figure 18:
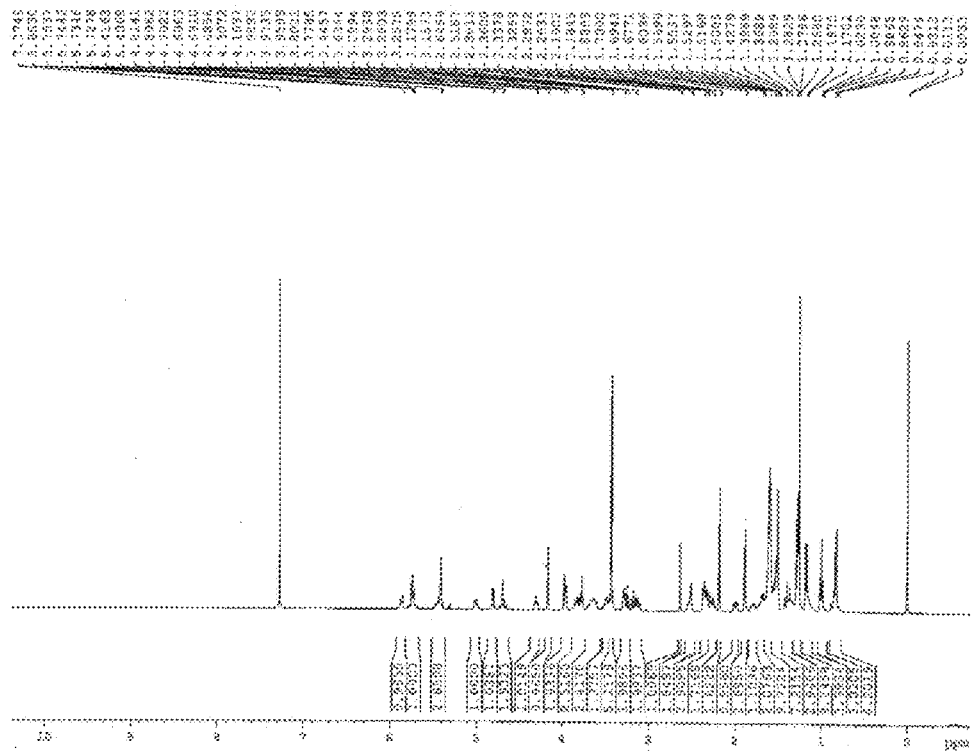
FIG. 18: The $^1$H-NMR spectrum of tenvermectin B dissolved in $CDCl_3$.
Figure 19:
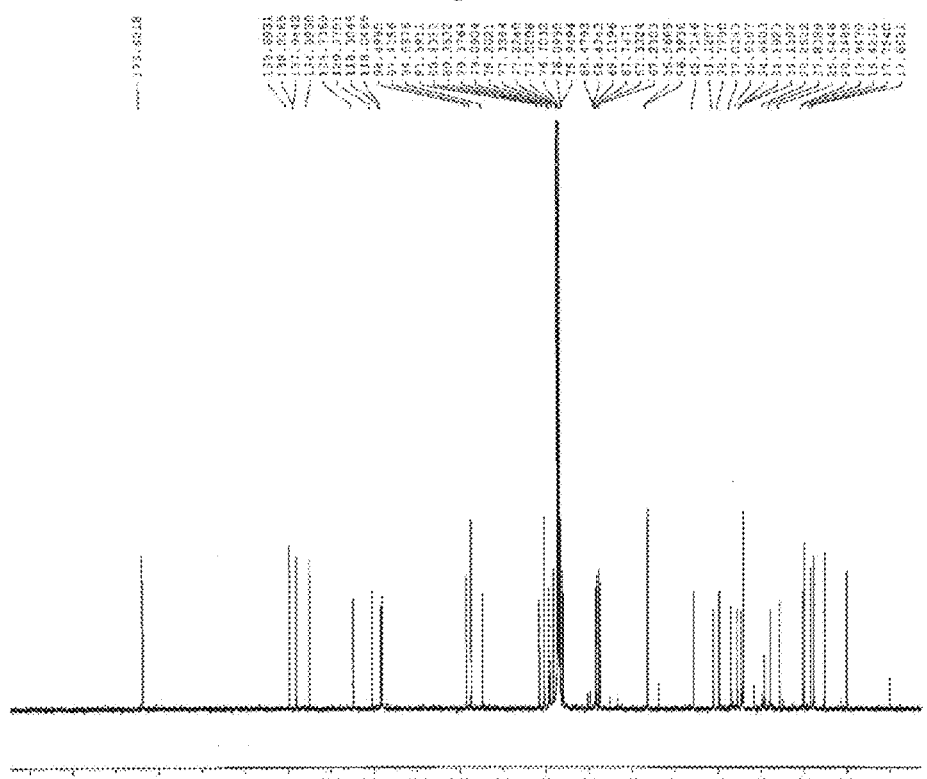
FIG. 19: The $^{13}$C-NMR spectrum of tenvermectin B dissolved in $CDCl_3$.
Figure 20:
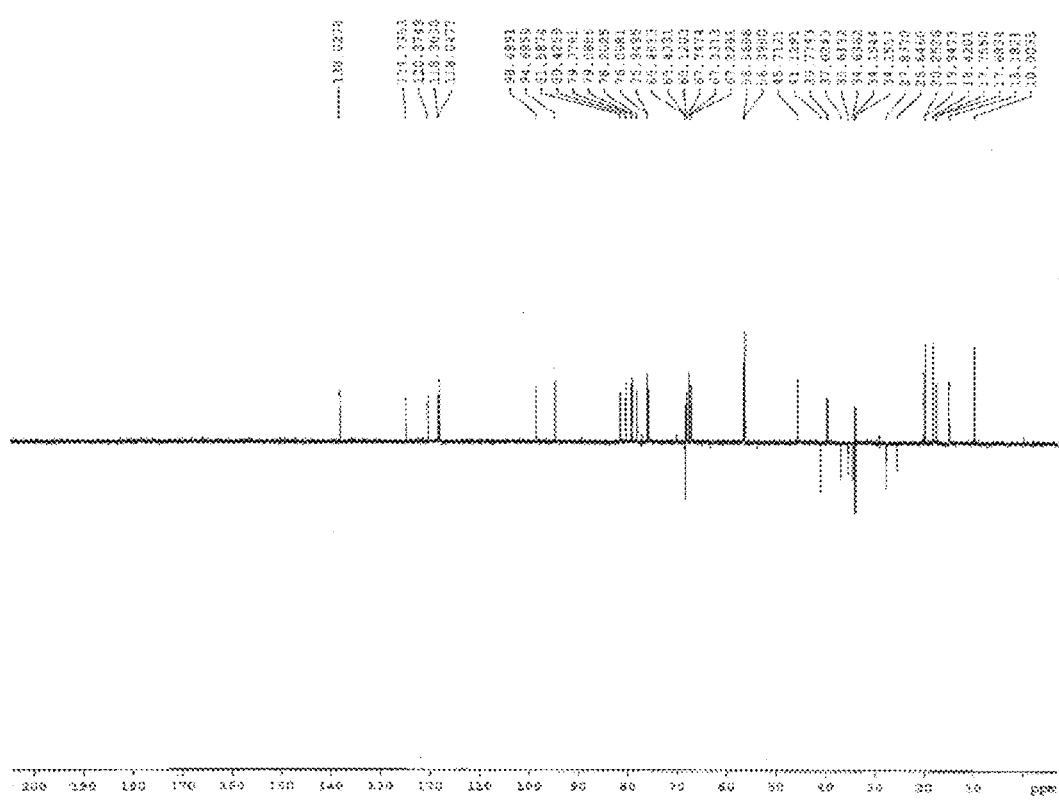
FIG. 20: The DEPT135 spectrum of tenvermectin B dissolved in $CDCl_3$.

12. Fermentation and HPLC analysis of genetically engineered strain MA220: The method was the same as that of step 5 of the present Example. HPLC results are shown in FIG. 12: A is the HPLC chromatogram of the fermentation sample of the genetically engineered strain MA220, B is the HPLC chromatogram of the fermentation sample of the genetically engineered strain AD28. The results show that the fermentation product of genetically engineered strain MA220 produces two obviously new compounds (The retention times of which in the Figure are 8.773 and 11.066, respectively).

Example 2 Extraction and Identification of the Fermentation Product of Genetically Engineered Strain MA220

The fermentation broth was filtered with a filter cloth to obtain a filter cake, which was extracted with ethanol twice to obtain an ethanol extract. The ethanol extract was concentrated to dryness under vacuum to obtain an extractum comprising tenvermectin A and B. After mixing the extractum with silica gel, the extractum was applied on silica gel column and gradiently eluted with 90:10, 80:20, 70:30, 60:40 petroleum ether/acetone. The eluted fractions were collected fractionally, detected by TLC, resulting in an eluent containing two target components, which was concentrated to dryness under vacuum. The above components were separated by reverse chromatography under the following conditions:

Liquid phase system: Agilent 1100 semi-preparative high pressure liquid chromatography Chromatographic column: ZORBAX.Eclipse XDB-C18 (250 mm*9.4 mm)

Eluent: methanol/acetonitrile/water=46:46:8

Flow rate: 1.5 mL/min

Detection wavelength: λ=240 nm

The peak with a retention time of 17.1 min was collected to give Compound 1; the peak with a retention time of 21.5 min was collected to give compound 2.

The mass spectrometry analysis as well as NMR analysis spectra of Compound 1 and Compound 2 are shown in FIGS. 13-20. The results show that: the molecular weight is 832 and 846, respectively. The results of structural analysis show that they have the structures showed by tenvermectin as above, and the two components are tenvermectin A (TEVA) and tenvermectin B (TEVB).

Example 3 Yield and Stability Test of Genetically Engineered Strain MA220

The spores of genetically engineered strain MA220 were diluted gradiently and spread onto YMS culture medium, cultured at 28° C. for 6-8 d, so that single colonies were grown out. Fifteen single colonies in relatively consistent morphology (i.e., single colonies that were capable of producing spores that were gray rather than white or partial black, and the colony sizes thereof were relatively consistent) were randomly selected, numbered as MA220-1 to MA220-15, spotted on YMS plates, cultured at 28° C. for 6-8 d. The colonies were basically the same size, i.e. between 0.7-0.8 cm. These single colonies were fermented according to the method of Example 1, step 5, and the seed liquids corresponding to each of the single colonies were inoculated to 3 bottled fermentation medium for implementing parallel test thereon; meanwhile, the control i.e. MA220-CK was set, i.e. the fermentation was implemented with the lawn of MA220 on YMS plates. The fermentation results were tested by HPLC, and the titers were calculated by taking the sample obtained in Example 2 as the reference standard. The results are shown in Table 1.

TABLE 1

| Strain Number | Fermentation pH | TEVA Fermentation Unit (µg/ml) | TEVB Fermentation Unit (µg/ml) | Total Fermentation Unit (µg/ml) | Average Fermentation Unit (µg/ml) |
|---|---|---|---|---|---|
| MA220-1 | 7.31 | 994 | 321 | 1315 | 1322 |
|  | 7.27 | 993 | 317 | 1310 |  |
|  | 7.33 | 1014 | 327 | 1341 |  |
| MA220-2 | 7.17 | 1122 | 362 | 1484 | 1421 |
|  | 7.21 | 1089 | 347 | 1436 |  |
|  | 7.17 | 1021 | 323 | 1344 |  |
| MA220-3 | 7.06 | 1004 | 320 | 1324 | 1386 |
|  | 7.04 | 1081 | 343 | 1424 |  |
|  | 7.07 | 1076 | 336 | 1412 |  |
| MA220-4 | 7.06 | 1070 | 335 | 1405 | 1307 |
|  | 7.07 | 972 | 310 | 1282 |  |
|  | 7.03 | 930 | 305 | 1235 |  |
| MA220-5 | 7.05 | 1025 | 330 | 1355 | 1412 |
|  | 7.1 | 1102 | 347 | 1449 |  |
|  | 7.05 | 1088 | 345 | 1433 |  |
| MA220-6 | 7.04 | 1096 | 343 | 1439 | 1454 |
|  | 7.04 | 1079 | 343 | 1421 |  |
|  | 7.03 | 1139 | 364 | 1503 |  |
| MA220-7 | 7.12 | 1063 | 392 | 1455 | 1436 |
|  | 7.14 | 1040 | 406 | 1446 |  |
|  | 7.14 | 1023 | 383 | 1406 |  |
| MA220-8 | 7.14 | 1095 | 388 | 1483 | 1459 |
|  | 7.13 | 1113 | 386 | 1499 |  |
|  | 7.14 | 1023 | 371 | 1394 |  |
| MA220-9 | 7.14 | 1049 | 337 | 1387 | 1412 |
|  | 7.14 | 1043 | 369 | 1412 |  |
|  | 7.14 | 1089 | 348 | 1437 |  |
| MA220-10 | 7.15 | 1180 | 376 | 1555 | 1545 |
|  | 7.14 | 1160 | 367 | 1527 |  |
|  | 7.14 | 1185 | 367 | 1553 |  |
| MA220-11 | 7.13 | 1128 | 386 | 1514 | 1527 |
|  | 7.13 | 1100 | 403 | 1502 |  |
|  | 7.13 | 1157 | 408 | 1566 |  |
| MA220-12 | 7.14 | 1156 | 392 | 1548 | 1531 |
|  | 7.13 | 1114 | 388 | 1502 |  |
|  | 7.12 | 1148 | 395 | 1544 |  |
| MA220-13 | 7.17 | 887 | 340 | 1227 | 1136 |
|  | 7.18 | 765 | 303 | 1069 |  |
|  | 7.19 | 805 | 308 | 1113 |  |
| MA220-14 | 7.16 | 790 | 296 | 1086 | 1113 |
|  | 7.16 | 894 | 327 | 1221 |  |
|  | 7.17 | 749 | 284 | 1033 |  |
| MA220-15 | 7.14 | 1027 | 407 | 1434 | 1479 |
|  | 7.12 | 1085 | 403 | 1487 |  |
|  | 7.12 | 1120 | 395 | 1516 |  |
| MA220-CK | 7.15 | 1088 | 394 | 1481 | 1437 |
|  | 7.19 | 1082 | 397 | 1479 |  |
|  | 7.14 | 974 | 376 | 1350 |  |

The results show that the fermentation of genetically engineered strain MA220 is relatively stable: the final pH values of fermentation are between 7.0-7.3, the ratio of TEVA/TEVB is about 3/1, and the total fermentation titer is basically above 1300 m/ml.

Example 4 Biological Activity of Tenvermectins Against Pests and Harmful Mites

1. Indoor activity assay of tenvermectins against *Tetranychus cinnabarinus*: The indoor activity of tenvermectins were assayed, wherein *Tetranychus cinnabarinus* was used as the test insect, avermectins were used as the control medicament, and the activities of tenvermectins and avermectins were compared.

Test organism: *Tetranychus cinnabarinus*: inoculated onto horsebean seedling for culture under the conditions of artificial climate-room [(26±1)° C., RH (70±5)%, H/D14].

Test medicaments: 96% avermectins (Hebei Veyong Bio-Chemical Co., Ltd.), 98% tenvermectins (TEVA:TEVB=8:2 (weight ratio)) (prepared according to the method of Example 2 of the present invention): 1 g 96% avermectins and 98% tenvermectins were weighted into the beaker, and 93 g methanol and 6 g emulsifier OP10 were added to prepare a preparation having a concentration of 10000 mg/L, which was diluted with water to prepare a liquid medicament for test having a concentration of 0.005, 0.01, 0.025, 0.05 mg/L.

Experimental Methods: a method of leaf discs-dipping insects-immersion was adopted: Adult mites that were kept indoors and had consistent physiological conditions were selected. Horsebean leaves with consistent growth were selected, and made into leaf discs with a diameter of 2 cm by a puncher. The leaf discs were placed onto the absorbent cottons at the center of plastic dishes in a manner of back up, wherein each of the dishes had 3 leaf discs. The adult mites were inoculated onto the leaf discs with a small brush, wherein each of the leaf discs were inoculated with 30 adult mites. Appropriate amount of water was added, and the plastic dishes were placed into the culture chamber at (26±1)° C. with a light intensity of 3000~4500lx, 14 h/d, and a RH of 50%~75%. Two hours later, the number of adult mites was checked under a stereoscopic microscope: the number of mites on leaf discs of each of the dishes was not less than 20. The prepared medicament having a mass concentration of 0.005, 0.01, 0.025, 0.05 mg/L was placed into beakers, and the leaves, nipped by forceps, were successively dipped into the medicament from low concentration to high concentration (dipping time was 5 s). The control was as follows: female adult mites were treated with distilled water, wherein each mass concentration was for one treatment, and each treatment was repeated for three times. After the medicament on leaves was dried by airing, the treated leaf discs were placed into an artificial climate-room at (26±1)° C. and a photoperiod of 14 h and cultured for 24 h. The Petri dishes were added with a small amount of water to keep moisture.

After medicament dipping, the mites were very active, but began to slow down their activities 5-8 h after treatment, and became stationary after 12-24 h.

Death criteria: The mite bodies were gently touched with a brush during inspection, and completely immobile mites were judged to death.

The results are shown in Table 2:

TABLE 2

Activity of tenvermectins and avermectins against *Tetranychus cinnabarinus*

| Medicament | Toxicity regression equation (y=) | LC50/ (mg · L-1) | Correlation coefficient | 95% Confidence limit/ (mg · L-1) |
|---|---|---|---|---|
| avermectins | 10.0483 + 2.4238X | 0.0083 | 0.9105 | 0.01 |
| tenvermectins | 12.3248 + 3.1721x | 0.0049 | 0.9304 | 0 |

The results show that the LC50 of tenvermectins against *Tetranychus cinnabarinus* is 0.0049 mg/L, and the LC50 of avermectins against *Tetranychus cinnabarinus* is 0.0083 mg/L, i.e. the activity of tenvermectins against *Tetranychus cinnabarinus* are higher than that of avermectins.

2. Activity assay of tenvermectins against bollworms and armyworms: Activity of tenvermectins were assayed, wherein bollworms and armyworms were used as test insects, and milbemycins and avermectins were used as the control medicaments.

Test organism: bollworms (*Helicoverpa armigera* Hubner), 3 instar larvae; armyworms (*Mythimna separate* Walker), 3 instar larvae.

Test medicaments: 0.5% tenvermectins emulsifiable concentrate, 2% milbemycins emulsifiable concentrate, 0.5% avermectins emulsifiable concentrate.

| Preparations | Active Ingredients | Solvents | Emulsifiers |
|---|---|---|---|
| 0.5% tenvermectins emulsifiable concentrate | tenvermectins: 0.5 g | methanol: 94.5 g | polyoxyethylene nonylphenol ether: 5.0 g |
| 2% milbemycins emulsifiable concentrate | milbemycins: 2.0 g | methanol: 93.0 g | polyoxyethylene nonylphenol ether: 5.0 g |
| 0.5% avermectins emulsifiable concentrate | avermectins: 0.5 g | ethyl acetate: 91.5 g | polyoxyethylene lauryl ether: 8.0 g |

The medicaments were diluted with water to a certain concentration for test.

Test Methods: The gastric toxicity of the test medicaments against the test insects were assayed by the method of feeding the insects with feed-medicament mixture.

Test results: The activities of the test medicaments against 3 instar bollworms and 3 instar armyworms are shown in Table 3 and Table 4.

TABLE 3

The activities of the test medicaments against 3 instar bollworms

| Medicament | Concentration mg/L | 24h Mortality (%) | Remarks |
|---|---|---|---|
| 0.5% tenvermectins emulsifiable concentrate | 500 | 100 | the method of feeding the insects with feed-medicament mixture was repeated for twice, with 3 repeats per treatment each time |
|  | 100 | 100 |  |
|  | 50 | 95 |  |
|  | 25 | 60 |  |
| 2% milbemycins emulsifiable concentrate | 2000 | 100 |  |
|  | 400 | 80 |  |
|  | 200 | 50 |  |
|  | 100 | 20 |  |
| 0.5% avermectins emulsifiable concentrate | 100 | 80 |  |
|  | 50 | 50 |  |
|  | 25 | 30 |  |

TABLE 4

The activities of the test medicaments against 3 instar armyworms

| Medicament | Concentration mg/L | 24 h Mortality (%) | Remarks |
|---|---|---|---|
| 0-5% tenvermectins emulsifiable concentrate | 500 | 100 | the method of small leaf discs addition was implemented for once, with 3 repeats per treatment each time |
|  | 100 | 100 |  |
|  | 50 | 90 |  |
|  | 25 | 50 |  |
| 2% milbemycins emulsifiable concentrate | 2000 | 100 |  |
|  | 400 | 90 |  |
|  | 200 | 60 |  |
|  | 100 | 40 |  |
| 0.5% avermectins emulsifiable concentrate | 100 | 100 |  |
|  | 50 | 90 |  |
|  | 25 | 60 |  |

Experimental results show that, under the same medicament concentration, the activities of tenvermectins against bollworms and armyworms are higher than those of milbemycins, and are similar as those of avermectins.

3. Activity assay of tenvermectins against pine wood nematodes: The indoor activities of sixteen-membered macrolide compounds such as tenvermectins, avermectins, ivermectin, milbemycins, emamectin benzoate were assayed, wherein pine wood nematodes were used as the test insects. The aim was to compare the difference in activities of such medicaments on pine wood nematodes.

Test medicaments: five kinds of medicaments, i.e. 0.5% avermectins emulsifiable concentrate, 0.5% tenvermectins emulsifiable concentrate, 0.5% ivermectin emulsifiable concentrate, 2% milbemycins emulsifiable concentrate, 2.5% emamectin benzoate microemulsion.

Test Method: The immersion method was adopted. Five mass concentrations 2, 5, 10, 20, 50 mg/L were set for each of the medicaments, and each concentration was repeated for three times. The experimental results were subjected to statistics after 24 h (see Table 5).

TABLE 5

Toxicity assay of several sixteen-membered macrolide compounds against pine wood nematodes

| Medicaments | Mortality at different concentrations (mg/L, %) | | | | | LC50 (mg/L) |
|---|---|---|---|---|---|---|
|  | 2 | 5 | 10 | 20 | 50 |  |
| Tenvermectins | 66.67 | 89.36 | 90.14 | 97.14 | 100 | 1.9154 |
| Emamectin Benzoate | 48.27 | 61.68 | 67.44 | 75 | 86.67 | 2.8055 |
| Ivermectin | 18.52 | 42.55 | 57.47 | 58.33 | 78.94 | 11.0629 |
| Avermectins | 43.24 | 46.07 | 63.1 | 66.94 | 78.02 | 5.3479 |
| Milbemycins | 40.54 | 52.08 | 65.52 | 65.32 | 72.93 | 5.0123 |
| CK |  |  | 4.83 |  |  | — |

The experimental results show that, among the tested sixteen-membered macrolide compounds, tenvermectins have the highest activity against pine wood nematodes.

REFERENCES

1. Sambrook J, Fritsh E, Maniatis T. Molecular cloning: A Laboratory Manual. 3rd ed, New York: Cold Spring Harbor Laboratory Press, 2002.
2. Gust B, Kiser T, Chater K F. REDIRECT Technology: PCR-targeting system in *streptomyces coelicolor*. Norwich: John Innes Centre. 2002.
3. Kieser T, Bibb M J, Buttner M J et al. Practical *Streptomyces* Genetics. Norwich: The John Innes Foundation, 2000.

| Preparations | Active Ingredients | Solvents | Emulsifiers |
|---|---|---|---|
| 0.5% tenvermectins emulsifiable concentrate | tenvermectins: 0.5 g | methanol: 94.5 g | polyoxyethylene nonylphenol ether: 5.0 g |
| 2% milbemycins emulsifiable concentrate | milbemycins: 2.0 g | methanol: 93.0 g | polyoxyethylene nonylphenol ether: 5.0 g |
| 0.5% avermectins emulsifiable concentrate | avermectins: 0.5 g | ethyl acetate: 91.5 g | polyoxyethylene lauryl ether: 8.0 g |
| 0.5% ivermectin emulsifiable concentrate | ivermectin: 0.5 g | methanol: 94.5 g | polyoxyethylene nonylphenol ether: 5.0 g |
| 2.5% emamectin benzoate microemulsion | emamectin benzoate: 2.5 g | n-butyl alcohol: 5.0 g; water: 87.5 g | polyoxyethylene alkylphenol ether phosphate: 5.0 g |

4. Haiyang Xia, Jun Huang, Minjie Hu, etc., Construction of an ordered cosmid library of *S. avermitilis* for genetic modification of the industrial strains, Chinese Journal of Antibiotics, 2009, 34 (7): 403-405.

The invention claimed is:

1. A recombinant *Streptomyces* expressing tenvermectin A or tenvermectin B, wherein the recombinant *Streptomyces*
   (1) has an inactivated or activity-decreased aveD gene, has an inactivated or activity-decreased aveAI gene, and has a functional milAI gene; or
   (2) has an inactivated or activity-decreased aveAI gene, and has a functional milAI gene.

2. The recombinant *Streptomyces* according to claim 1, wherein the recombinant *Streptomyces* is *Streptomyces avermitilis*.

3. A method for producing tenvermectin A or tenvermectin B, the method comprising: culturing the recombinant *Streptomyces* of claim 1, and recovering tenvermectin A or tenvermectin B from the culture.

4. A method for constructing the recombinant *Streptomyces* of claim 1, said method comprising:
   providing a *Streptomyces* to be modified; and
   inactivating the aveAI gene in the *Streptomyces* to be modified or decreasing the activity thereof, and introducing the functional milAI gene into the *Streptomyces* to be modified.

5. The method according to claim 4, wherein the *Streptomyces* to be modified is *Streptomyces avermitilis*.

* * * * *

```
                            SEQUENCE LISTING

<160> NUMBER OF SEQ ID NOS: 23

<210> SEQ ID NO 1
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 1
atgcccagcc ccgcacaggt gatccgggag atcgcccggg tgctccgccc cggcggccgg     60
ctggccgtca cggacgtcgc a                                               81

<210> SEQ ID NO 2
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 2
attccgggga tccgtcgacc tgcagttcga agttcctatt ctctagaaag tataggaact     60
tcgaagcagc tccagcctac a                                               81

<210> SEQ ID NO 3
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 3
tccttcgacg cggcgtgggc cctggagtgt ctcctgcaca ttccggggat ccgtcgacc      59

<210> SEQ ID NO 4
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 4
ctccccgcgc ttcatgccgg tccgcccgaa ggcgcgcagt gtaggctgga gctgcttc       58

<210> SEQ ID NO 5
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 5
aagttccctt cccatgcccg gccattg                                         27

<210> SEQ ID NO 6
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 6
```
attccggcgt actcgtcgat gtgcaccagg                                           30

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
cgggcgatct cccggatcac ctgtg                                                25

<210> SEQ ID NO 8
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 8
cagaccatgt ggctcgtgga gc                                                   22

<210> SEQ ID NO 9
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 9
atgcatcagg agaggccgag gtcgttc                                              27

<210> SEQ ID NO 10
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 10
atgcatcacg ggtcatccgg cgttgaagcg                                           30

<210> SEQ ID NO 11
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 11
aagcttgagg ggcgagaagg actggtcggg c                                         31

<210> SEQ ID NO 12
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 12
accggacgcc tgccactccg cccgtatc                                             28

<210> SEQ ID NO 13
<211> LENGTH: 33
<212> TYPE: DNA
<213> ORGANISM: Artificial Sequence

```
<220> FEATURE:
<223> OTHER INFORMATION: Synthetic Polynucleotide

<400> SEQUENCE: 13
atttaaatgc ctgtgtccgc tccgacgatc gcc                              33

<210> SEQ ID NO 14
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 14
tcgaccaccc cacgcccgac gaactc                                      26

<210> SEQ ID NO 15
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 15
cgaccacgtc agcgcctcca tcgacac                                     27

<210> SEQ ID NO 16
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 16
aacctgcaga acatcgctcc cgccccg                                     27

<210> SEQ ID NO 17
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 17
aacaagctta tttaaatccg acggcttgtc cacgtgc                          37

<210> SEQ ID NO 18
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 18
aacgaattct gcgagtcgcg acactggc                                    28

<210> SEQ ID NO 19
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 19
aacggtacct caccgctagg caatgctcg                                   29
```

```
<210> SEQ ID NO 20
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 20
gggaggagtt gctggagctg ctgggg                                         26

<210> SEQ ID NO 21
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 21
gtggccaact cgggtgacat gggtcg                                         26

<210> SEQ ID NO 22
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 22
tgcatctgac cgcctacgcc caaccg                                         26

<210> SEQ ID NO 23
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 23
gcgtcggcaa accggtcgta gacccc                                         26
```